United States Patent
Bian et al.

(10) Patent No.: US 12,139,468 B2
(45) Date of Patent: *Nov. 12, 2024

(54) METHODS FOR PREPARING SUBSTITUTED CHROMANONE DERIVATIVES

(71) Applicant: HANGZHOU DUYI TECHNOLOGY CO. LTD., Zhejiang (CN)

(72) Inventors: Gaofeng Bian, Hangzhou (CN); Zengying Zheng, Hangzhou (CN)

(73) Assignee: HANGZHOU DUYI TECHNOLOGY CO. LTD., Hangzhou (CN)

( * ) Notice: Subject to any disclaimer, the term of this patent is extended or adjusted under 35 U.S.C. 154(b) by 155 days.

This patent is subject to a terminal disclaimer.

(21) Appl. No.: 17/807,389

(22) Filed: Jun. 17, 2022

(65) Prior Publication Data

US 2022/0324825 A1 Oct. 13, 2022

Related U.S. Application Data

(63) Continuation of application No. 17/325,600, filed on May 20, 2021, now Pat. No. 11,377,434, which is a continuation of application No. PCT/CN2020/102931, filed on Jul. 20, 2020.

(51) Int. Cl.
*C07D 311/22* (2006.01)
*B01J 23/72* (2006.01)

(52) U.S. Cl.
CPC .............. *C07D 311/22* (2013.01); *B01J 23/72* (2013.01)

(58) Field of Classification Search
None
See application file for complete search history.

(56) References Cited

U.S. PATENT DOCUMENTS

| | | | |
|---|---|---|---|
| 4,716,238 A | 12/1987 | Timar et al. | |
| 2007/0225528 A1 | 9/2007 | Noyori et al. | |

FOREIGN PATENT DOCUMENTS

| | | |
|---|---|---|
| CN | 104447658 A | 3/2015 |
| CN | 107848943 A | 3/2018 |
| CN | 107849003 A | 3/2018 |
| EP | 0225217 A1 | 6/1987 |
| KR | 20170016754 A | 2/2017 |
| WO | 2008043019 A1 | 4/2008 |
| WO | 2016086674 A1 | 6/2016 |
| WO | 2017023123 A1 | 2/2017 |

OTHER PUBLICATIONS

International Search Report in PCT/CN2020/102931 mailed on Apr. 22, 2021, 4 pages.
Written Opinion in PCT/CN2020/102931 mailed on Apr. 22, 2021, 5 pages.
Cheng, Yijuan et al., Research Progress towards Copper-Catalyzed Coupling Reactions for C—N Bonds and C—O Bonds, Chinese Journal of Organic Chemistry, 33(5): 877-890, 2013, (Eng. abstract only).
Dai, Lixin, Ullmann Reaction, A Centennial Memory and Recent Renaissance-Related Formation of Carbon-Heteroatom Bond, Progress in Chemistry, 30(9): 1257-1297, 2018, (Eng. abstract only).
Liu, Yajun et al., Copper(II)-Catalyzed C—O Coupling of Aryl Bromides with Aliphatic Diols: Synthesis of Ethers, Phenols, and Benzo-Fused Cyclic Ethers, Organic & Biomolecular Chemistry, 12(26): 4747-4753, 2014.
Xia, Shanghua et al., Copper-Catalyzed Hydroxylation of (Hetero)aryl Halides under Mild Conditions, Journal of the American Chemical Society, 138(41): 13493-13496, 2016.
Sunil U. Tekale et al., Application Progress of Recent Advances in Some Copper Catalyzed Coupling Reactions, Mini-Reviews in Organic Chemistry, 10(3): 281-301, 2013.
Waldemar Adam et al., Synthetic Applications of Nonmetal Catalysts for Homogeneous Oxidations, Chem. Rev., 101(11): 3499-3548, 2001.
Takeshi Ohkuma et al., The Hydrogenation/Transfer Hydrogenation Network: Asymmetric Hydrogenation of Ketones with Chiral η6-Arene/N-Tosylethylenediamine-Ruthenium(II) Catalysts, J. Am. Chem. Soc., 128(27): 8724-8725, 2006.
Decision of Patent Grant in Korean Application No. 10-2022-7014749 mailed on Nov. 24, 2022, 4 pages.

*Primary Examiner* — Po-Chih Chen
(74) *Attorney, Agent, or Firm* — METIS IP LLC

(57) ABSTRACT

The present disclosure relates to a method for preparing a compound of formula (I).

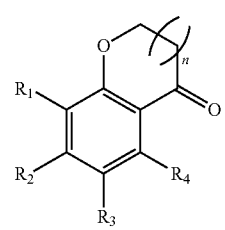

(I)

In the compound of formula (I), n may be 0 to 5 and each of $R_1$, $R_2$, $R_3$, and $R_4$ may be independently selected from the group consisting of H, —O-Alkyl, halo, alkyl, —CN, or —$NO_3$.

19 Claims, No Drawings

METHODS FOR PREPARING SUBSTITUTED CHROMANONE DERIVATIVES

CROSS-REFERENCE TO RELATED APPLICATIONS

This application is a continuation of U.S. patent application Ser. No. 17/325,600, filed on May 20, 2021, which is a continuation of International Application No. PCT/CN2020/102931, filed on Jul. 20, 2020, the entire contents of each of which are hereby incorporated by reference.

TECHNICAL FIELD

The present disclosure generally relates to pharmaceutical preparation technology, and in particular, to methods for preparing substituted chromanone derivatives.

BACKGROUND

Chromanone and chromanone derivatives (e.g., substituted chromanone derivatives) are natural compounds that are involved in various biological activities, such as but not limited to anti-inflammatory activities, anti-allergic activities, anti-cancer activities, anti-platelet aggregation activities, and antibacterial activities. Chromanone and chromanone derivatives are also active ingredients of a plurality of traditional Chinese medicines and have important significance in the preparation of medicines. Conventionally, the chromanone and chromanone derivatives are synthesized from substituted phenols or substituted cresols.

For example, as disclosed in WO2008043019, sodium 3-(2-Fluoro-phenoxy)-propionic acid was prepared by reacting 2-Fluoro-phenol and 3-Bromo propionic acid in the presence of a base (e.g., NaOH). Further, sodium 3-(2-Fluoro-phenoxy)-propionic acid was acidified with hydrochloric acid to obtain 3-(2-Fluoro-phenoxy)-propionic acid. Then, 3-(2-Fluoro-phenoxy)-propionic acid was dehydrated and cyclized in the presence of concentrated sulfuric acid to 8-Fluoro-4-chromanone.

As another example, as disclosed in KR2017016754, 3-(3,5-Difluoro-phenoxy)-propan-1-ol was prepared by reacting 3,5-Difluoro-phenol and 3-Chloro-propan-1-ol in the presence of NaH. Further, 3-(3,5-Difluoro-phenoxy)-propan-1-ol was oxidized to 3-(3,5-Difluoro-phenoxy)-propionic acid by concentrated sulfuric acid. Then, 3-(3,5-Difluoro-phenoxy)-propionic acid was dehydrated and cyclized to 5,7-Difluoro-4-chromanone.

However, in these cases, as raw materials for preparing substituted chromanone derivatives, substituted phenol is expensive, which increases the cost of preparing the substituted chromanone derivatives. Therefore, it is desirable to provide improved methods for preparing substituted chromanone derivatives, thereby reducing the cost of preparing the substituted chromanone derivatives, improving the efficiency of preparing substituted chromanone derivatives and the yield of substituted chromanone derivatives.

SUMMARY

An aspect of the present disclosure relates to a method for preparing a compound of formula (I):

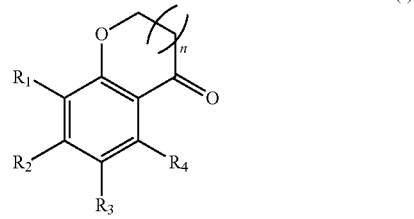

In the compound of formula (I), n may be 0 to 5 and each of $R_1$, $R_2$, $R_3$, and $R_4$ may be independently selected from the group consisting of H, —O-Alkyl, halo, alkyl, —CN, or —$NO_3$. The method may include treating a compound of formula (II),

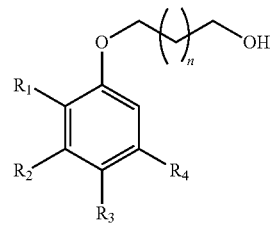

In the compound of formula (II), n, $R_1$, $R_2$, $R_3$, and $R_4$ may be as defined above. The compound of formula (II) may be prepared by reacting a compound of formula (III)

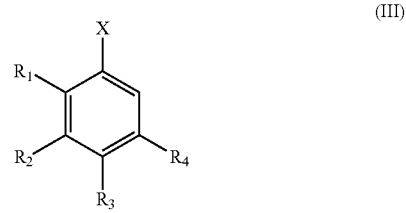

with a compound of formula (IV)

in the presence of a catalyst and a base. In the compound of formula (III), $R_1$, $R_2$, $R_3$, and $R_4$ may be as defined above and X may be halo. In the compound of formula (IV), n may be as defined above and $R_5$ may be H, —$CH_3$, or —$CH_2CH_3$. The catalyst may include a ligand and a copper compound.

In some embodiments, the copper compound may be $Cu(acac)_2$, CuCl, CuBr, CuI, $CuCl_2$, $CuBr_2$, $CuI_2$, CuO, $Cu_2O$, CuOH, Cu(OH)Cl, $Cu(OH)_2$, CuS, $Cu_2S$, $Cu_2SO_3$, $CuSO_4$, $Cu_2P_2O_7$, $Cu_3(PO_4)_2$, CuSCN, $Cu(CO_2CH_3)_2$, $Cu(CO_2CH_3)_2 \cdot H_2O$, $Cu(CO_3)_2$, $Cu(NO_3)_2$, $Cu(NO)_2$, Nano-copper, CuO—ZnO, CuO—$Al_2O_3$, CuO—$Cr_2O_3$, CuO/$SiO_2$, Cu, Cu—Zn/Al, Cu—Zn—Zr, Cu—Cr, Cu—Zn—Al, CuMP, CuXnLm, or $Cu(phen)Cl_2$, or a mixture of at least two of $Cu(acac)_2$, CuCl, CuBr, CuI, $CuCl_2$, $CuBr_2$, $CuI_2$, CuO, $Cu_2O$, CuOH, Cu(OH)Cl, $Cu(OH)_2$, CuS, $Cu_2S$, Cu$_2$SO$_3$, CuSO$_4$, Cu$_2$P$_2$O$_7$, Cu$_3$(PO$_4$)$_2$, CuSCN, Cu(CO$_2$CH$_3$)$_2$, Cu(CO$_2$CH$_3$)$_2$H$_2$O, Cu(CO$_3$)$_2$, Cu(NO$_3$)$_2$, Cu(NO)$_2$, Nano-copper, CuO—ZnO, CuO—Al$_2$O$_3$, CuO—Cr$_2$O$_3$, CuO/SiO$_2$, Cu, Cu—Zn/Al, Cu—Zn—Zr, Cu—Cr, Cu—Zn—Al, CuMP, CuXnLm, Cu(phen)Cl$_2$.

In some embodiments, the ligand may be a compound of formula (V).

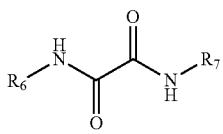
(V)

In the compound of formula (V), each of R$_6$ and R$_7$ may be independently selected from the group consisting of H, alkyl, and aryl.

In some embodiments, the aryl may be independently selected from the group consisting of phenyl, thienyl, pyrrolyl, substituted phenyl, hydroxy-phenyl, and substituted phenol.

In some embodiments, the ligand may be a compound of formula (Va)

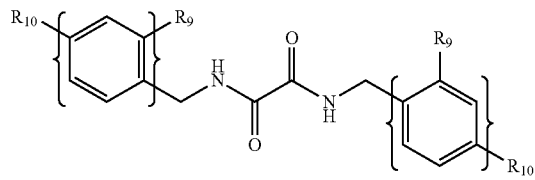
(Va)

or a compound of formula (Vb),

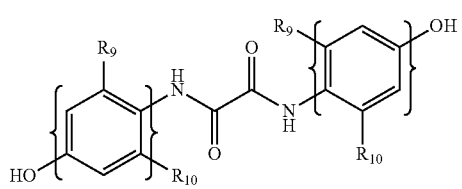
(Vb)

In the compound of formula (Va) and the compound of formula (Vb), each of R$_9$ and R$_{10}$ may be independently selected from the group consisting of H, and alkyl.

In some embodiments, the ligand may be a compound of formula (VI),

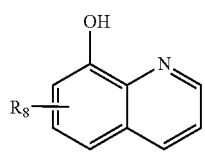
(VI)

a compound of formula (VII),

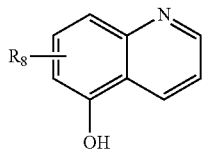
(VII)

a compound of formula (VIII),

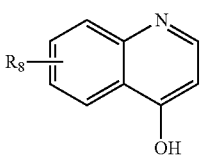
(VIII)

a compound of formula (IX),

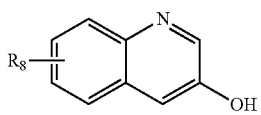
(IX)

or a compound of formula (X),

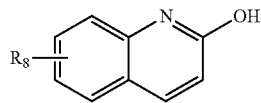
(X)

wherein R$_8$ may be H, alkyl, or aryl.

In some embodiments, the base may be NaOH, KOH, K$_2$CO$_3$, Na$_2$CO$_3$, KTB, NaTB, LiOH, Cs$_2$CO$_3$, or a mixture of at least two of NaOH, KOH, K$_2$CO$_3$, Na$_2$CO$_3$, KTB, NaTB, LiOH, Cs$_2$CO$_3$.

In some embodiments, the compound of formula (I) may be prepared by treating a compound of formula (XI)

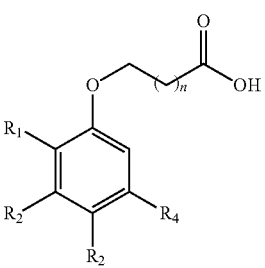
(XI)

in the presence of concentrated sulfuric acid. In the compound of formula (XI), n, R$_1$, R$_2$, R$_3$, and R$_4$ may be as defined above.

In some embodiments, the compound of formula (XI) may be prepared by treating the compound of formula (II) in the presence of tempo, NaClO, and NaClO$_2$.

In some embodiments, the compound of formula (I) may be treated to prepare a compound of formula (XII)

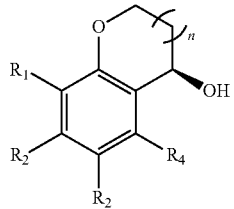
(XII)

or an enantiomer of the compound of formula (XII), wherein n, $R_1$, $R_2$, $R_3$, and $R_4$ may be as defined above.

In some embodiments, $R_1$ and $R_3$ may be H, and $R_2$ and $R_4$ may be the same haloes.

In some embodiments, $R_1$, $R_2$, and $R_4$ may be H, and $R_3$ may be halo.

In some embodiments, $R_2$, $R_3$, and $R_4$ may be H, and $R_1$ may be halo.

A further aspect of the present disclosure relates to a method for preparing a compound of formula (I):

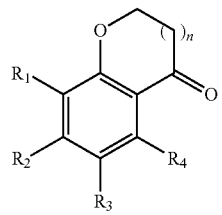
(I)

In the compound of formula (I), n may be 0 to 5 and each of $R_1$, $R_2$, $R_3$, and $R_4$ may be independently selected from the group consisting of H, —O-Alkyl, halo, alkyl, —CN, or —$NO_3$. The method may include treating a compound of formula (XI)

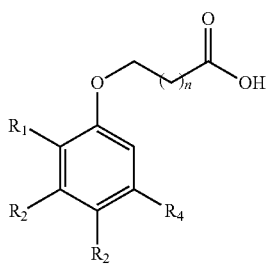
(XI)

in the presence of concentrated sulfuric acid. In the compound of formula (XI), n, $R_1$, $R_2$, $R_3$, and $R_4$ may be as defined above. The compound of formula (XI) may be prepared by treating a compound of formula (II)

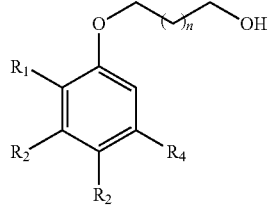
(II)

in the presence of tempo, NaClO, and $NaClO_2$. In the compound of formula (II), n, $R_1$, $R_2$, $R_3$, and $R_4$ may be as defined above. The compound of formula (II) may be prepared by reacting a compound of formula (III),

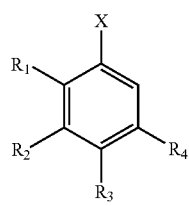
(III)

with a compound of formula (IV),

(IV)

in the presence of a catalyst and a base. In the compound of formula (III), $R_1$, $R_2$, $R_3$, and $R_4$ may be as defined above and X may be halo. In the compound of formula (IV), n may be as defined above and $R_5$ may be H, —$CH_3$, or —$CH_2CH_3$. The catalyst may include a ligand and a copper compound.

In some embodiments, the copper compound may be $Cu(acac)_2$, CuCl, CuBr, CuI, $CuCl_2$, $CuBr_2$, $CuI_2$, CuO, $Cu_2O$, CuOH, Cu(OH)Cl, $Cu(OH)_2$, CuS, $Cu_2S$, $Cu_2SO_3$, $CuSO_4$, $Cu_2P_2O_7$, $Cu_3(PO_4)_2$, CuSCN, $Cu(CO_2CH_3)_2$, $Cu(CO_2CH_3)_2H_2O$, $Cu(CO_3)_2$, $Cu(NO_3)_2$, $Cu(NO)_2$, Nano-copper, CuO—ZnO, CuO—$Al_2O_3$, CuO—$Cr_2O_3$, CuO/$SiO_2$, Cu, Cu—Zn/Al, Cu—Zn—Zr, Cu—Cr, Cu—Zn—Al, CuMP, CuXnLm, or $Cu(phen)Cl_2$, or a mixture of at least two of $Cu(acac)_2$, CuCl, CuBr, CuI, $CuCl_2$, $CuBr_2$, $CuI_2$, CuO, $Cu_2O$, CuOH, Cu(OH)Cl, $Cu(OH)_2$, CuS, $Cu_2S$, $Cu_2SO_3$, $CuSO_4$, $Cu_2P_2O_7$, $Cu_3(PO_4)_2$, CuSCN, $Cu(CO_2CH_3)_2$, $Cu(CO_2CH_3)_2H_2O$, $Cu(CO_3)_2$, $Cu(NO_3)_2$, $Cu(NO)_2$, Nano-copper, CuO—ZnO, CuO—$Al_2O_3$, CuO—$Cr_2O_3$, CuO/$SiO_2$, Cu, Cu—Zn/Al, Cu—Zn—Zr, Cu—Cr, Cu—Zn—Al, CuMP, CuXnLm, $Cu(phen)Cl_2$. The ligand may be a compound of formula (V),

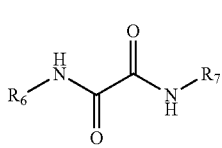
(V)

In the compound of formula (V), each of $R_6$ and $R_7$ may be independently selected from the group consisting of H, alkyl, and aryl. The aryl may be independently selected from the group consisting of phenyl, thienyl, pyrrolyl, substituted phenyl, hydroxy-phenyl, and substituted phenol.

In some embodiments, the ligand may be a compound of formula (Va)

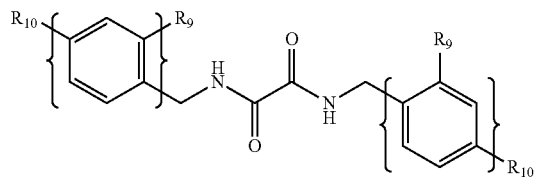

(Va)

or a compound of formula (Vb).

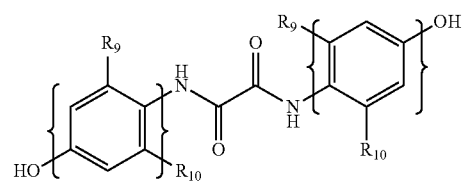

(Vb)

In the compound of formula (Va) or the compound of formula (Vb), each of $R_9$ and $R_{10}$ may be independently selected from the group consisting of H, and alkyl.

In some embodiments, the ligand may be a compound of formula (VI),

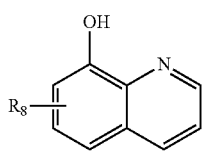

(VI)

a compound of formula (VII),

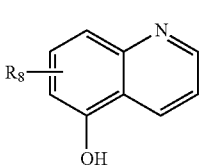

(VII)

a compound of formula (VIII),

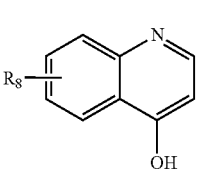

(VIII)

a compound of formula (IX),

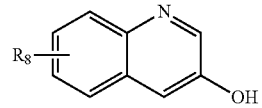

(IX)

or a compound of formula (X),

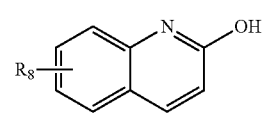

(X)

wherein $R_8$ may be H, alkyl, or aryl.

In some embodiments, n may be 1, $R_1$ and $R_3$ may be H, and $R_2$ and $R_4$ may be the same haloes; $R_1$, $R_2$, and $R_4$ may be H, and $R_3$ may be halo, or $R_2$, $R_3$, and $R_4$ may be H, and $R_1$ may be halo.

In some embodiments, to prepare the compound of formula (II), the compound of formula (III) and the compound of formula (IV) may be reacted at a temperature of 100-125° C., and the molar yield may be at least 65%.

In some embodiments, to prepare the compound of formula (XI), the compound of formula (II) may be treated at a temperature of 30-40° C., and the molar yield may be at least 85%.

In some embodiments, to prepare the compound of formula (I), the compound of formula (XI) may be treated at a temperature of 20-30° C., and the molar yield may be at least 85%.

A still further aspect of the present disclosure relates to a compound of formula (I).

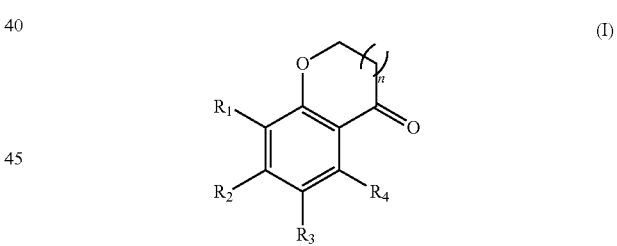

(I)

In the compound of formula (I), n is 0 to 5 and each of $R_1$, $R_2$, $R_3$, and $R_4$ may be independently selected from the group consisting of H, —O-Alkyl, halo, alkyl, —CN, or —NO$_3$. The compound of formula (I) may be prepared by treating a compound of formula (II).

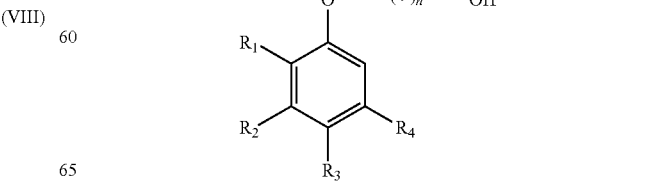

(II)

In the compound of formula (II), n, $R_1$, $R_2$, $R_3$, and $R_4$ may be as defined above. The compound of formula (II) may be prepared by reacting a compound of formula (III)

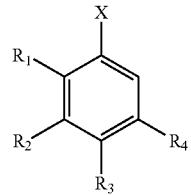

with a compound of formula (IV)

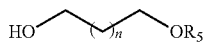

in the presence of a catalyst and a base. In the compound of formula (III), $R_1$, $R_2$, $R_3$, and $R_4$ may be as defined above and X may be halo. In the compound of formula (IV), n may be as defined above and $R_5$ may be H, —$CH_3$, and —$CH_2CH_3$. The catalyst may include a ligand and a copper compound.

A still further aspect of the present disclosure relates to a compound of formula (I).

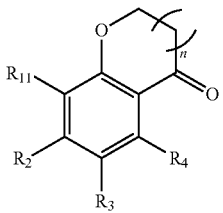

In the compound of formula (I), n is 0 to 5 and each of $R_1$, $R_2$, $R_3$, and $R_4$ may be independently selected from the group consisting of H, —O-Alkyl, halo, alkyl, —CN, or —$NO_3$. The compound of formula (I) may be prepared by treating a compound of formula (XI)

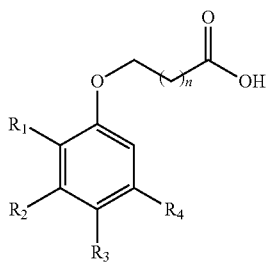

in the presence of concentrated sulfuric acid. In the compound of formula (XI), n, $R_1$, $R_2$, $R_3$, and $R_4$ may be as defined above. The compound of formula (XI) may be prepared by treating a compound of formula (II)

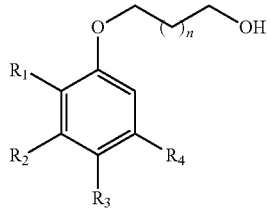

in the presence of tempo, NaClO, and $NaClO_2$. In the compound of formula (II), n, $R_1$, $R_2$, $R_3$, and $R_4$ may be as defined above. The compound of formula (II) may be prepared by treating a compound of formula (III)

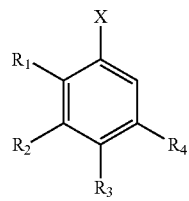

with a compound of formula (IV),

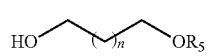

in the presence of a catalyst and a base. In the compound of formula (III), $R_1$, $R_2$, $R_3$, and $R_4$ may be as defined above and X may be halo. In the compound of formula (IV), n may be as defined above and $R_5$ may be H, —$CH_3$, and —$CH_2CH_3$. The catalyst may include a ligand and a copper compound.

Additional features will be set forth in part in the description which follows, and in part will become apparent to those skilled in the art upon examination of the following or may be learned by production or operation of the examples. The features of the present disclosure may be realized and attained by practice or use of various aspects of the methodologies, instrumentalities, and combinations set forth in the detailed examples discussed below.

DETAILED DESCRIPTION

The following description is presented with a combination of specific embodiments, and it should be noted that descriptions and embodiments given herein are merely for the purposes of describing the specific embodiments of the present disclosure, to make features of the embodiments of the present disclosure more readily understood, and are not intended to be limiting the scope of the claims.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

As used herein, the term "alkyl," employed alone or in combination with other terms, refers to a saturated hydrocarbon group that may be straight-chain or branched. In some embodiments, the alkyl group contains 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethyl propyl, and the like. In some embodiments, the alkyl group is methyl, ethyl, or propyl.

As used herein, the term "aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylene diphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted. In certain embodiments, "aryl" means phenyl or naphthyl, each optionally substituted. In many embodiments, "aryl" is optionally substituted phenyl.

As used herein, "halo" or "halogen," employed alone or in combination with other terms, includes fluoro, chloro, bromo, and iodo. In some embodiments, halo is F, Cl, or Br.

As used herein, the term "substituted" as used herein means that any one or more hydrogens on the designated atom, radical or moiety are replaced with a selection from the indicated group, provided that the atom's normal valence is not exceeded, and that the substitution results in an acceptably stable compound.

As used herein, the term "stereoisomer" is a general term for all isomers of individual molecules that differ only in the orientation of their atoms in space. It includes enantiomers and isomers of compounds with more than one chiral center that are not mirror images of one another (diastereoisomers).

As used herein, the terms "enantiomer" and "enantiomeric" refer to a molecule that cannot be superimposed on its mirror image and hence is optically active, wherein the enantiomer rotates the plane of polarized light in one direction and its mirror image compound rotates the plane of polarized light in the opposite direction.

The heteroatom or the group having a heteroatom may include but not limited to a halogen (—F, —Cl, —Br, —I), hydroxyl (—OH), carboxyl (—COOH), acyl (—CO—), acyloxy (—COO—), amino (—NH$_2$), alkylamino (—NHR), dialkylamino (—NR$_1$R$_2$), arylamino (—NHAr), amide (—CONH$_2$), ester (—COOR), carboxamide (—CONR$_1$R$_2$), carbamate (—NHCOOR), alkoxyl (—OR), aryloxy (—OAr), alkylthio (—SR), arylthio (—SAr), alkyl sulfonate (—OSO$_2$R), nitro (—NO$_2$), cyano (—CN), isocyano (—NC), oxo (=O), azo (—N=N—), thiol (—SH), sulfonyl (—SO$_2$R), phosphono (—PO(OR$_1$)(OR$_2$)), phosphinyl (

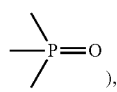

), a thioester (—NCS), thioalkoxy (—OCSR), thiocyanate (—SCN), isothiocyanate (—NCS), a phosphate ester or salt (—OP(O)(OH)$_2$), a sulfate ester or salt (—OSO$_2$(OH)), or a combination thereof.

A method for preparing a compound (i.e., a substituted chromanone derivative) of formula (I) may be illustrated in the following scheme 1:

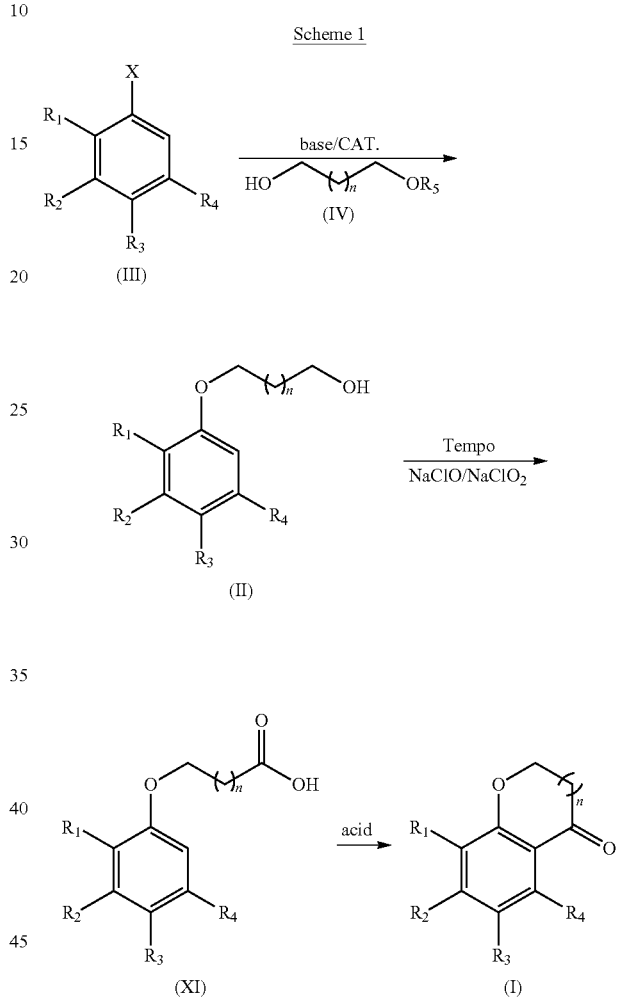

In the compound of formula (I), each of R$_1$, R$_2$, R$_3$, and R$_4$ may be independently selected from the group consisting of H, —O-alkyl, halo, alkyl, —CN, or —NO$_3$. In some embodiments, the alkyl may include, but are not limited to, methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethyl propyl, and the like. In some embodiments, the halo may be F, Cl, Br, and I.

In the compound of formula (I), n may be 0 to 5. In certain preferred embodiments, n may be 1-4. In certain preferred embodiments, n may be 2-3. In certain preferred embodiments, n may be 1.

In some embodiments, R$_1$ and R$_3$ may be the same groups, and R$_2$ and R$_4$ may be the same groups. In certain preferred embodiments, R$_1$ and R$_3$ may be H, and R$_2$ and R$_4$ may be the same groups. In this embodiment, the compound of formula (I) may be a compound of formula (Ia):

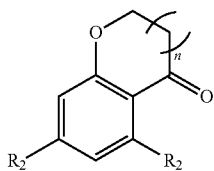
(Ia)

In certain preferred embodiments, $R_1$ and $R_3$ may be H, and $R_2$ and $R_4$ may be the same halo. In certain preferred embodiments, $R_1$ and $R_3$ may be H, and $R_2$ and $R_4$ may be F. When $R_1$ and $R_3$ are H, and $R_2$ and $R_4$ are F, the compound of formula (I) may be a compound of formula ($Ia_1$):

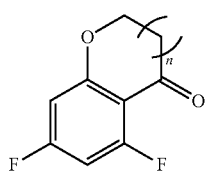
($Ia_1$)

In certain preferred embodiments, $R_1$ and $R_3$ may be H, $R_2$ and $R_4$ may be F, and n may be 1. When $R_1$ and $R_3$ are H, $R_2$ and $R_4$ are F, and n is 1, the compound of formula (I) may be a compound of formula ($Ia_2$):

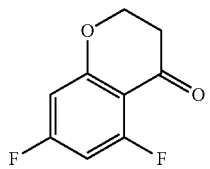
($Ia_2$)

In some embodiments, $R_1$ and $R_3$ may be the same groups, and $R_2$ and $R_4$ may be different groups. In certain preferred embodiments, $R_1$ and $R_3$ may be H, and $R_2$ and $R_4$ may be different groups. In this embodiment, the compound of formula (I) may be a compound of formula (Ib):

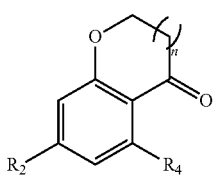
(Ib)

In certain preferred embodiments, $R_1$ and $R_3$ may be H, and $R_2$ and $R_4$ may be different haloes. In certain preferred embodiments, $R_1$ and $R_3$ may be H, $R_2$ may be Cl, and $R_4$ may be F. When $R_1$ and $R_3$ are H, $R_2$ is Cl, and $R_4$ is F, the compound of formula (I) may be a compound of formula ($Ib_1$)

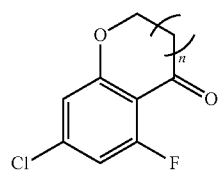
($Ib_1$)

or an isomer ($Ib_1'$)

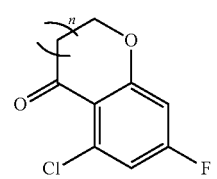
($Ib_1'$)

of the compound of formula ($Ib_1$). In certain preferred embodiments, $R_1$ and $R_3$ may be H, $R_2$ may be Cl, and $R_4$ may be F, and n may be 1. When $R_1$ and $R_3$ are H, $R_2$ is Cl, and $R_4$ is F, and n is 1, the compound of formula (I) may be a compound of formula ($Ib_2$)

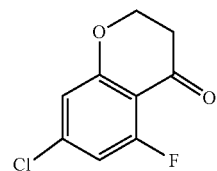
($Ib_2$)

or an isomer ($Ib_2'$)

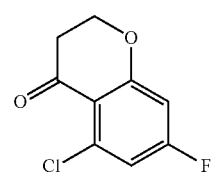
($Ib_2'$)

of the compound of formula ($Ib_2$).

In some embodiments, $R_1$, $R_2$, and $R_4$ may be the same groups. In certain preferred embodiments, $R_1$, $R_2$, and $R_4$ may be H. In this embodiment, the compound of formula (I) may be a compound of formula (Ic):

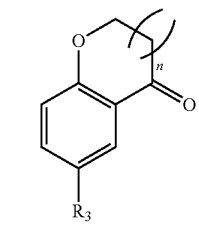
(Ic)

In certain preferred embodiments, $R_1$, $R_2$, and $R_4$ may be H, and $R_3$ may be a halo. In certain preferred embodiments, $R_1$, $R_2$, and $R_4$ may be H, and $R_3$ may be F. When $R_1$, $R_2$, and $R_4$ are H, and $R_3$ is F, the compound of formula (I) may be a compound of formula ($Ic_1$):

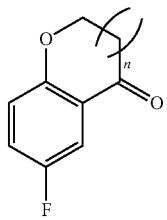

($Ic_1$)

In certain preferred embodiments, $R_1$, $R_2$, and $R_4$ may be H, $R_3$ may be F, and n may be 1. When $R_1$, $R_2$, and $R_4$ are H, $R_3$ is F, and n is 1, the compound of formula (I) may be a compound of formula ($Ic_2$):

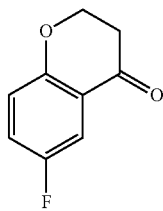

($Ic_2$)

In some embodiments, $R_2$, $R_3$, and $R_4$ may be the same groups. In certain preferred embodiments, $R_2$, $R_3$, and $R_4$ may be H. In this embodiment, the compound of formula (I) may be a compound of formula (Id):

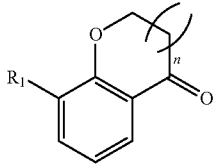

(Id)

In certain preferred embodiments, $R_2$, $R_3$, and $R_4$ may be H, and $R_1$ may be a halo. In certain preferred embodiments, $R_2$, $R_3$, and $R_4$ may be H, and $R_1$ may be F. When $R_2$, $R_3$, and $R_4$ are H, and $R_1$ is F, the compound of formula (I) may be a compound of formula ($Id_1$):

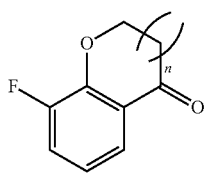

($Id_1$)

In certain preferred embodiments, $R_2$, $R_3$, and $R_4$ may be H, $R_1$ may be F, and n may be 1. When $R_2$, $R_3$, and $R_4$ are H, $R_1$ is F, and n is 1, the compound of formula (I) may be a compound of formula ($Id_2$):

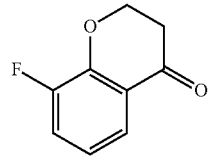

($Id_2$)

In one aspect of the present disclosure, the compound of formula (I) may be prepared by treating the acid having formula (XI)

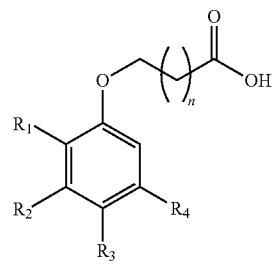

(XI)

in the presence of an acid. In some embodiments, the acid may be concentrated sulfuric acid.

In the process of preparing the compound of formula (I), the n, $R_1$, $R_2$, $R_3$, and $R_4$ may be as stated above. For example, when $R_1$ and $R_3$ are H, and $R_2$ and $R_4$ are the same groups, the compound of formula (XI) may be a compound of formula (XIa):

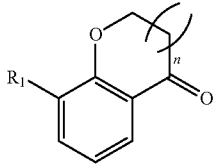

(XIa)

Preferably, when $R_1$ and $R_3$ are H, and $R_2$ and $R_4$ are F, the compound of formula (XI) may be a compound of formula ($XIa_1$):

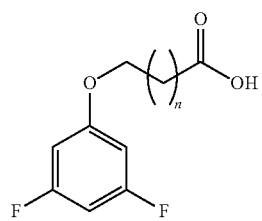

($XIa_1$)

Preferably, when $R_1$ and $R_3$ are H, $R_2$ and $R_4$ are F, and n is 1, the compound of formula (XI) may be a compound of formula ($XIa_2$):

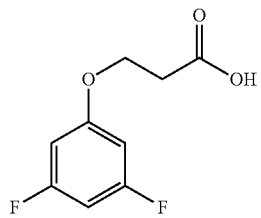

(XIa₂)

As another example, when $R_1$ and $R_3$ are H, and $R_2$ and $R_4$ are different groups, the compound of formula (XI) may be a compound of formula (XIb):

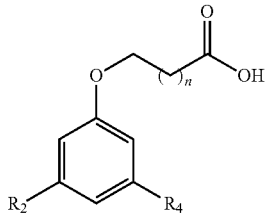

(XIb)

Preferably, when $R_1$ and $R_3$ are H, $R_2$ is Cl, and $R_4$ is F, the compound of formula (XI) may be a compound of formula (XIb₁):

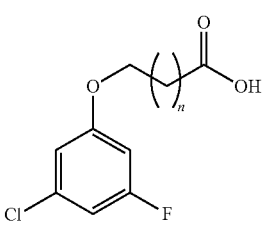

(XIb₁)

Preferably, when $R_1$ and $R_3$ are H, $R_2$ is Cl, $R_4$ is F, and n is 1, the compound of formula (XI) may be a compound of formula (XIb₂):

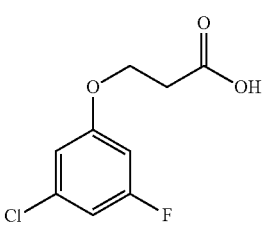

(XIb₂)

As a further example, when $R_1$, $R_2$, and $R_4$ are H, the compound of formula (XI) may be a compound of formula (XIc):

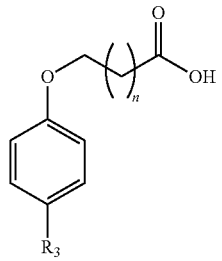

(XIc)

Preferably, when $R_1$, $R_2$, and $R_4$ are H, and $R_3$ is F, the compound of formula (XI) may be a compound of formula (XIc₁):

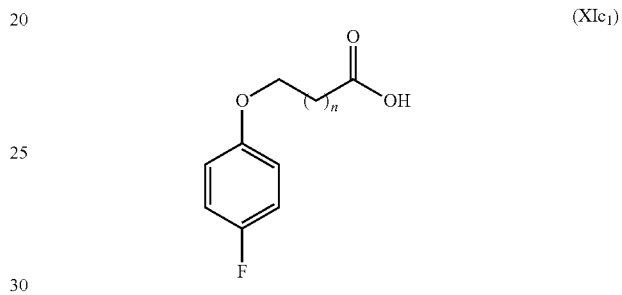

(XIc₁)

Preferably, when $R_1$, $R_2$, and $R_4$ are H, $R_3$ is F, and n is 1, the compound of formula (XI) may be a compound of formula (XIc₂):

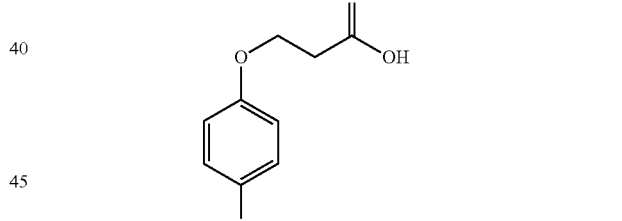

(XIc2)

As a still further example, when $R_2$, $R_3$, and $R_4$ are H, the compound of formula (XI) may be a compound of formula (XId):

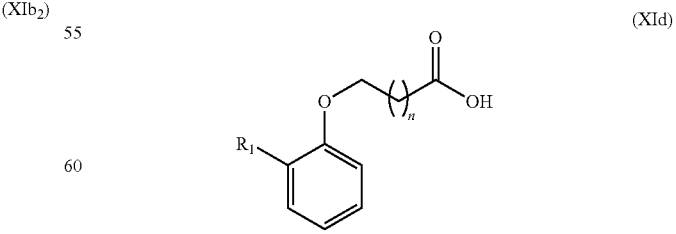

(XId)

Preferably, when $R_2$, $R_3$, and $R_4$ are H, and $R_1$ is F, the compound of formula(XI) may be a compound of formula (XId₁):

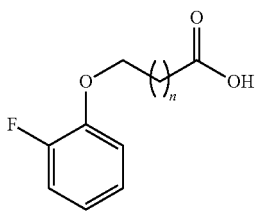

Preferably, when $R_2$, $R_3$, and $R_4$ are H, $R_1$ is F, and n is 1, the compound of formula (XI) may be a compound of formula (XId$_2$):

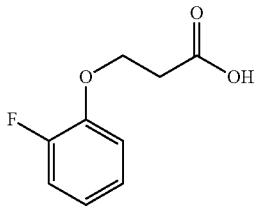

In a further aspect of the present disclosure, the compound of formula (XI) may be prepared by oxidizing the compound of formula (II)

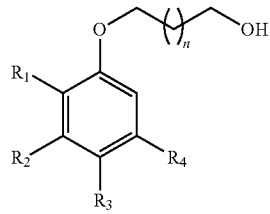

in the presence of an oxidant.

In the process of preparing the compound of formula (XI), the n, $R_1$, $R_2$, $R_3$, and $R_4$ may be as stated above for the process of preparing the compound of formula (I). For example, when $R_1$ and $R_3$ are H, and $R_2$ and $R_4$ are the same groups, the compound of formula (II) may be a compound of formula (IIa):

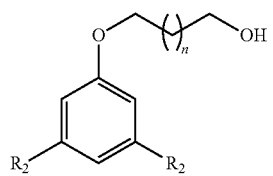

Preferably, when $R_1$ and $R_3$ are H, and $R_2$ and $R_4$ are F, the compound of formula (II) may be a compound of formula (IIa$_1$):

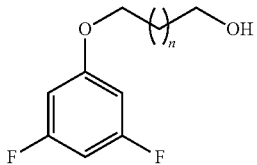

Preferably, when $R_1$ and $R_3$ are H, $R_2$ and $R_4$ are F, and n is 1, the compound of formula (II) may be a compound of formula (IIa$_2$):

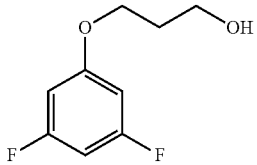

As another example, when $R_1$ and $R_3$ are H, and $R_2$ and $R_4$ are different groups, the compound of formula (II) may be a compound of formula (IIb):

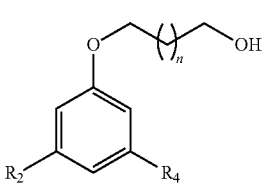

Preferably, when $R_1$ and $R_3$ are H, $R_2$ is Cl, and $R_4$ is F, the compound of formula (II) may be a compound of formula (IIb$_1$):

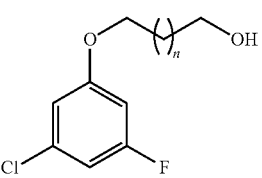

Preferably, when $R_1$ and $R_3$ are H, $R_2$ is Cl, $R_4$ is F, and n is 1, the compound of formula (II) may be a compound of formula (IIb$_2$):

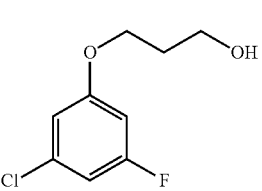

As a further example, when $R_1$, $R_2$, and $R_4$ are H, the compound of formula (II) may be a compound of formula (IIc):

(IIc)

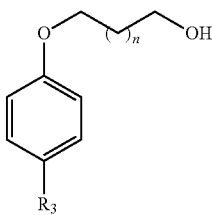

Preferably, when $R_1$, $R_2$, and $R_4$ are H, $R_3$ is F, the compound of formula (II) may be a compound of formula (IIc$_1$):

(IIc$_1$)

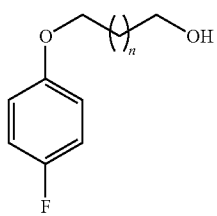

Preferably, when $R_1$, $R_2$, and $R_4$ are H, $R_3$ is F, and n is 1, the compound of formula (II) may be a compound of formula (IIc$_2$):

(IIc$_2$)

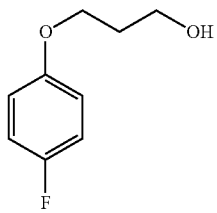

As a still further example, when $R_2$, $R_3$, and $R_4$ are H, the compound of formula(II) may be a compound of formula (IId):

(IId)

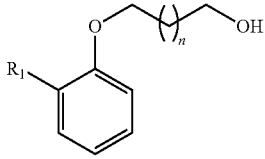

Preferably, when $R_2$, $R_3$, and $R_4$ are H, and $R_1$ is F, the compound of formula(II) may be a compound of formula (IId$_1$):

(IId$_1$)

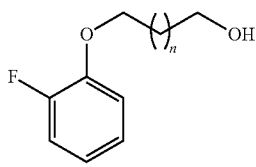

Preferably, when $R_2$, $R_3$, and $R_4$ are H, $R_1$ is F, and n is 1, the compound of formula(II) may be a compound of formula (IId$_2$):

(IId$_2$)

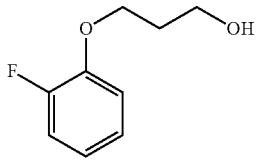

In some embodiments, the oxidant may include tempo, NaClO, and NaClO$_2$. Compared with concentrated sulfuric acid as an oxidant (e.g., as disclosed in KR2017016754), the oxidant used in the process of preparing the compound of formula (XI) is more environmentally friendly. In addition, when the concentrated sulfuric acid is used as the oxidant, a reaction temperature for preparing the compound of formula (XI) must be controlled at room temperature. The high reaction temperature may carbonize the product (i.e., the compound of formula (XI)) and reduce the yield of the product.

In a further aspect of the present disclosure, the compound of formula (II) may be prepared by reacting a compound of formula (III), (III)

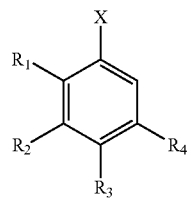

with a compound of formula (IV)

(IV)

in the presence of a catalyst and a base.

In the process of preparing the compound of formula (II), the $R_1$, $R_2$, $R_3$, and $R_4$ may be as stated above for the process of preparing the compound of formula (I). In the compound of formula (III), X may be a halo. In some embodiments, the halo may be F, Cl, Br, or I. In some embodiments, when $R_1$ and $R_3$ are H, and $R_2$ and $R_4$ are the same groups, the compound of formula (III) may be a compound of formula (IIIa):

(IIIa)

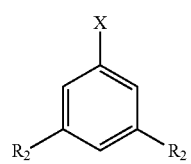

In certain preferred embodiments, when $R_1$ and $R_3$ are H, $R_2$ and $R_4$ are F, and X is Br, the compound of formula (III) may be 1-Bromo-3,5-difluorobenzene. In certain preferred embodiments, when $R_1$ and $R_3$ are H, $R_2$ and $R_4$ are F, and X is Cl, the compound of formula (III) may be 1-Chloro-3,5-difluorobenzene. In certain preferred embodiments, when $R_1$ and $R_3$ are H, $R_2$ and $R_4$ are F, and X is I, the compound of formula (III) may be 1,3-Difluoro-5-iodobenzene.

In some embodiments, when $R_1$ and $R_3$ are H, and $R_2$ and $R_4$ are different groups, the compound of formula (III) may be a compound of formula (IIIb):

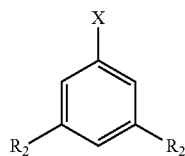

(IIIb)

In certain preferred embodiments, when $R_1$ and $R_3$ are H, $R_2$ is Cl, and $R_4$ is F, and X is Br, the compound of formula (III) may be 1-Bromo-3-chloro-5-fluoro-benzene.

In some embodiments, when $R_1$, $R_2$, and $R_4$ are H, the compound of formula (III) may be a compound of formula (IIIc):

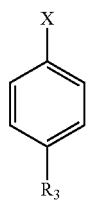

(IIIc)

In certain preferred embodiments, when $R_1$, $R_2$, and $R_4$ are H, $R_3$ is F, and X is Br, the compound of formula (III) may be 4-Bromofluorobenzene. In certain preferred embodiments, when $R_1$, $R_2$, and $R_4$ are H, $R_3$ is F, and X is Cl, the compound of formula (III) may be 4-Chlorofluorobenzene. In certain preferred embodiments, when $R_1$, $R_2$, and $R_4$ are H, $R_3$ is F, and X is I, the compound of formula (III) may be 1-Fluoro-4-iodobenzene.

In some embodiments, when $R_2$, $R_3$, and $R_4$ are H, the compound of formula (III) may be a compound of formula (IIId):

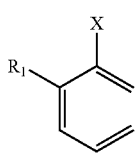

(IIId)

In certain preferred embodiments, when $R_2$, $R_3$, and $R_4$ are H, $R_1$ is F, and X is Br, the compound of formula (III) may be 2-Bromofluorobenzene. In certain preferred embodiments, when $R_2$, $R_3$, and $R_4$ are H, $R_1$ is F, and X is Cl, the compound of formula (III) may be 2-Chlorofluorobenzene. In certain preferred embodiments, when $R_2$, $R_3$, and $R_4$ are H, $R_1$ is F, and X is I, the compound of formula (III) may be 1-Fluoro-2-iodobenzene.

In the present disclosure, substituted halobenzene of formula (III) has the same $R_2$ and $R_4$ or substituent (e.g., (IIIc), (IIId)) is located at the para or ortho position of the halobenzene, which may ensure that the substituted chromanone derivative (i.e., the compound of formula (I)) prepared based on the substituted halobenzene is free of isomers, thereby improving the purity of the prepared substituted chromanone derivative.

In the present disclosure, as raw materials for preparing substituted chromanone derivatives (i.e., the compound of formula (I)), substituted halobenzenes (i.e., the compound of formula (III)) are cheaper than substituted phenols (e.g., as disclosed in WO2008043019 and KR2017016754), which reduces the cost of preparing the substituted chromanone derivatives.

In the compound of formula (IV), n may be as stated above for the process of preparing the compound of formula (I), and $R_5$ may be H, —$CH_3$, or —$CH_2CH_3$. In some embodiments, when n is 1 and $R_5$ is H, the compound of formula (IV) may be 1,2-Propanediol. In certain preferred embodiments, when n is 1 and $R_5$ is —$CH_3$, the compound of formula (IV) may be 1-Methoxy-3-propanol. In certain preferred embodiments, when n is 1 and $R_5$ is —$CH_2CH_3$, the compound of formula (IV) may be 1-Ethoxy-3-propanol. In certain preferred embodiments, when n is 0 and $R_5$ is H, the compound of formula (IV) may be ethylene glycol. In certain preferred embodiments, when n is 0 and $R_5$ is —$CH_3$, the compound of formula (IV) may be 2-Methoxyethanol. In certain preferred embodiments, when n is 0 and $R_5$ is —$CH_2CH_3$, the compound of formula (IV) may be 2-ethoxyethanol. In certain preferred embodiments, when n is 2 and $R_5$ is H, the compound of formula (IV) may be 1,4-butanediol. In certain preferred embodiments, when n is 3 and $R_5$ is H, the compound of formula (IV) may be 1,5-pentanediol. In certain preferred embodiments, when n is 4 and $R_5$ is H, the compound of formula (IV) may be 1,6-hexanediol. In certain preferred embodiments, when n is 5 and $R_5$ is H, the compound of formula (IV) may be 1,7-heptanediol.

In the process of preparing the compound of formula (II), the base may be NaOH, KOH, $K_2CO_3$, $Na_2CO_3$, KTB, NaTB, LiOH, $Cs_2CO_3$, or a mixture of at least two of NaOH, KOH, $K_2CO_3$, $Na_2CO_3$, KTB, NaTB, LiOH, $Cs_2CO_3$. In certain preferred embodiments, the base may be NaOH.

In the process of preparing the compound of formula (II), the catalyst may include a ligand and a copper compound. In some embodiments, the copper compound may include $Cu(acac)_2$, CuCl, CuBr, CuI, $CuCl_2$, $CuBr_2$, $CuI_2$, CuO, $Cu_2O$, CuOH, Cu(OH)Cl, $Cu(OH)_2$, CuS, $Cu_2S$, $Cu_2SO_3$, $CuSO_4$, $Cu_2P_2O_7$, $Cu_3(PO_4)_2$, CuSCN, $Cu(CO_2CH_3)_2$, $Cu(CO_2CH_3)_2 \cdot H_2O$, $Cu(CO_3)_2$, $Cu(NO_3)_2$, $Cu(NO)_2$, Nano-copper, CuO—ZnO, CuO—$Al_2O_3$, CuO—$Cr_2O_3$, CuO/$SiO_2$, Cu, Cu—Zn/Al, Cu—Zn—Zr, Cu—Cr, Cu—Zn—Al, CuMP, CuXnLm, or Cu(phen)$Cl_2$, or the like, or any combination thereof. For example, the copper compound may be a mixture of at least two of $Cu(acac)_2$, CuCl, CuBr, CuI, $CuCl_2$, $CuBr_2$, $CuI_2$, CuO, $Cu_2O$, CuOH, Cu(OH)Cl, $Cu(OH)_2$, CuS, $Cu_2S$, $Cu_2SO_3$, $CuSO_4$, $Cu_2P_2O_7$, $Cu_3(PO_4)_2$, CuSCN, $Cu(CO_2CH_3)_2$, $Cu(CO_2CH_3)_2 \cdot H_2O$, $Cu(CO_3)_2$, $Cu(NO_3)_2$, $Cu(NO)_2$, Nano-copper, CuO—ZnO, CuO—$Al_2O_3$, CuO—$Cr_2O_3$, CuO/$SiO_2$, Cu, Cu—Zn/Al, Cu—Zn—Zr, Cu—Cr, Cu—Zn—Al, CuMP, CuXnLm, Cu(phen)$Cl_2$. In certain preferred embodiments, the copper compound may be $Cu(acac)_2$, CuCl, CuBr, CuI, or Cu, or any combination thereof. For example, the copper compound may be a mixture of at least two of $Cu(acac)_2$, CuCl, CuBr, CuI, Cu.

In some embodiments, the catalyst may be a compound of formula (V).

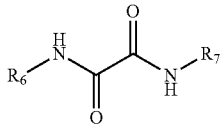

(V)

In the compound of formula (V), each of $R_6$ and $R_7$ may be independently selected from the group consisting of H, alkyl, and aryl. In some embodiments, the alkyl may be as stated above for the process of preparing the compound of formula (I). In some embodiments, the aryl may include, but are not limited to, phenyl, naphthyl, phenanthryl, fluorenyl, indenyl, pentalenyl, azulenyl, oxydiphenyl, biphenyl, methylene diphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted. In certain preferred embodiments, the aryl may be independently selected from the group consisting of phenyl, thienyl, pyrrolyl, substituted phenyl, hydroxy-phenyl, and substituted phenol.

In certain preferred embodiments, $R_6$ and $R_7$ may be the same groups. When $R_6$ and $R_7$ are the same groups, the compound of formula (V) may be a compound of formula (Va)

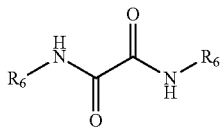

(Va)

For example, when $R_6$ and $R_7$ are H, the compound of formula (V) may be oxalamide. As another example, when $R_6$ and $R_7$ are phenyls, the compound of formula (V) may be N,N'-diphenyl-oxalamide. As a further example, when $R_6$ and $R_7$ are thienyls, the compound of formula (V) may be N,N'-Di-thiophen-2-yl-oxalamide or N,N'-Di-thiophen-3-yl-oxalamide. As still a further example, when $R_6$ and $R_7$ are pyrrolyls, the compound of formula (V) may be N,N'-Bis-(1H-pyrrol-3-yl)-oxalamide or N,N'-Bis-(1H-pyrrol-2-yl)-oxalamide. As still a further example, when $R_6$ and $R_7$ are hydroxy phenyls, the compound of formula (V) may be N,N'-Bis-(2-hydroxy-phenyl)-oxalamide, N,N'-Bis-(3-hydroxy-phenyl)-oxalamide, or N,N'-Bis-(4-hydroxy-phenyl)-oxalamide.

In certain preferred embodiments, when $R_6$ and $R_7$ are substituted phenyls, the ligand may be a compound of formula (Va).

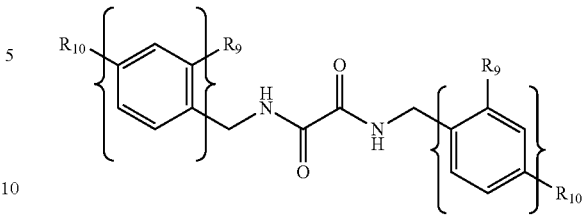

(Va)

Each of $R_9$ and $R_{10}$ may be independently selected from the group consisting of H, and alkyl. The alkyl may be as stated above. In certain preferred embodiments, $R_9$ and $R_{10}$ may be the same groups. For example, when $R_9$ and $R_{10}$ are methyls, the compound of formula (Va) may be N,N'-Bis-(2,4-dimethyl-benzyl)-oxalamide. In certain preferred embodiments, $R_9$ and $R_{10}$ may be the different groups. For example, when $R_9$ is methyl and $R_{10}$ is ethyl, the compound of formula (Va) may be N,N'-Bis-(4-ethyl-2-methyl-benzyl)-oxalamide. As another example, when $R_9$ is ethyl and $R_{10}$ is methyl, the compound of formula (Va) may be N,N'-Bis-(2-ethyl-4-methyl-benzyl)-oxalamide.

In certain preferred embodiments, when $R_6$ and $R_7$ are substituted phenols, the ligand may be a compound of formula (Vb).

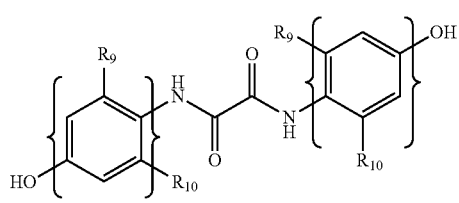

(Vb)

The $R_9$ and $R_{10}$ may be as stated above. In certain preferred embodiments, $R_9$ and $R_{10}$ may be the same groups. For example, when $R_9$ and $R_{10}$ are methyls, the compound of formula (Vb) may be N,N'-Bis-(4-hydroxy-2,6-dimethyl-phenyl)-oxalamide. In certain preferred embodiments, $R_9$ and $R_{10}$ may be the different groups. For example, when $R_9$ is methyl and $R_{10}$ is ethyl, the compound of formula (Vb) may be N,N'-Bis-(2-ethyl-4-hydroxy-6-methyl-phenyl)-oxalamide.

In certain preferred embodiments, $R_6$ and $R_7$ may be different groups. For example, when $R_6$ is H and $R_7$ is phenyl, the compound of formula (V) may be N-Phenyl-oxalamide. As another example, when $R_6$ is H and $R_7$ is thienyl, the compound of formula (V) may be N-thiophen-2-yl-oxalamide or N-thiophen-3-yl-oxalamide. As a further example, when $R_6$ is H and $R_7$ is pyrrolyl, the compound of formula (V) may be N-(1H-pyrrol-2-yl)-oxalamide or N-(1H-pyrrol-3-yl)-oxalamide. As still a further example, when $R_6$ is H and $R_7$ is hydroxy phenyl, the compound of formula (V) may be N-(2-Hydroxy-phenyl)-oxalamide, N-(3-Hydroxy-phenyl)-oxalamide, or N-(4-Hydroxy-phenyl)-oxalamide. As still a further example, when $R_6$ is methyl and $R_7$ is phenyl, the compound of formula (V) may be N-Methyl-N'-phenyl-oxalamide. As still a further example, when $R_6$ is methyl and $R_7$ is thienyl, the compound of formula (V) may be N-Methyl-N'-thiophen-2-yl-oxalamide or N-Methyl-N'-thiophen-3-yl-oxalamide. As still a further example, when $R_6$ is methyl and $R_7$ is pyrrolyl, the compound of formula (V) may be N-Methyl-N'-(1H-pyrrol-2-yl)-oxalamide or N-Methyl-N'-(1H-pyrrol-3-yl)-oxalamide. As still a further example, when $R_6$ is methyl and $R_7$ is hydroxy phenyl, the compound of formula (V) may be N-(2-Hydroxy-phenyl)-N'-methyl-oxalamide, N-(3-Hydroxy-phenyl)-N'-methyl-oxalamide, or N-(4-Hydroxy-phenyl)-N'-methyl-oxalamide.

In some embodiments, the catalyst may be a compound of formula (VI).

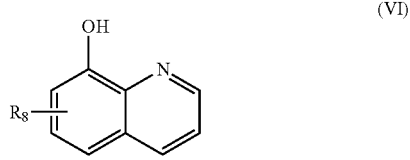

(VI)

In the compound of formula (VI), $R_8$ may be H, alkyl, or aryl. The alkyl and aryl may be as stated above. For example, when $R_8$ is H, the compound of formula (VI) may be quinolin-8-ol. As another example, when $R_8$ is methyl, the compound of formula (VI) may be 2-Methyl-quinolin-8-ol, 3-Methyl-quinolin-8-ol, 4-Methyl-quinolin-8-ol, 5-Methyl-quinolin-8-ol, 6-Methyl-quinolin-8-ol, or 7-Methyl-quinolin-8-ol. As a further example, when $R_8$ is phenyl, the compound of formula (VI) may be 2-Phenyl-quinolin-8-ol, 3-Phenyl-quinolin-8-ol, 4-Phenyl-quinolin-8-ol, 5-Phenyl-quinolin-8-ol, 6-Phenyl-quinolin-8-ol, or 7-Phenyl-quinolin-8-ol.

In some embodiments, the catalyst may be a compound of formula (VII).

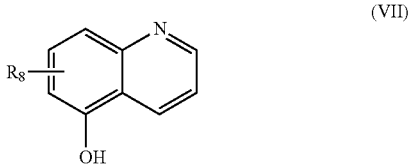

(VII)

The $R_8$ may be as stated above. For example, when $R^8$ is H, the compound of formula (VI) may be quinolin-5-ol. As another example, when $R_8$ is methyl, the compound of formula (VI) may be 2-Methyl-quinolin-5-ol, 3-Methyl-quinolin-5-ol, 4-Methyl-quinolin-5-ol, 6-Methyl-quinolin-5-ol, 7-Methyl-quinolin-5-ol, or 8-Methyl-quinolin-5-ol. As a further example, when $R_8$ is phenyl, the compound of formula (VI) may be 2-Phenyl-quinolin-5-ol, 3-Phenyl-quinolin-5-ol, 4-Phenyl-quinolin-5-ol, 6-Phenyl-quinolin-5-ol, 7-Phenyl-quinolin-5-ol, or 8-Phenyl-quinolin-5-ol.

In some embodiments, the catalyst may be a compound of formula (VIII).

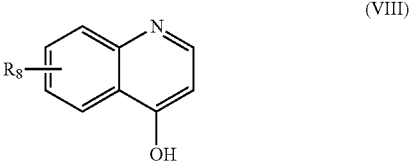

(VIII)

The $R_8$ may be as stated above. For example, when $R_8$ is H, the compound of formula (VI) may be quinolin-4-ol. As another example, when $R_8$ is methyl, the compound of formula (VI) may be 2-Methyl-quinolin-4-ol, 3-Methyl-quinolin-4-ol, 5-Methyl-quinolin-4-ol, 6-Methyl-quinolin-4-ol, 7-Methyl-quinolin-4-ol, or 8-Methyl-quinolin-4-ol. As a further example, when $R_8$ is phenyl, the compound of formula (VI) may be 2-Phenyl-quinolin-4-ol, 3-Phenyl-quinolin-4-ol, 5-Phenyl-quinolin-4-ol, 6-Phenyl-quinolin-4-ol, 7-Phenyl-quinolin-4-ol, or 8-Phenyl-quinolin-4-ol.

In some embodiments, the catalyst may be a compound of formula (IX),

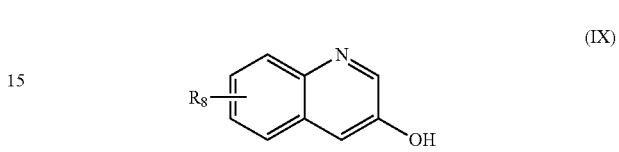

(IX)

The $R_8$ may be as stated above. For example, when $R_8$ is H, the compound of formula (VI) may be quinolin-3-ol. As another example, when $R_8$ is methyl, the compound of formula (VI) may be 2-Methyl-quinolin-3-ol, 4-Methyl-quinolin-3-ol, 5-Methyl-quinolin-3-ol, 6-Methyl-quinolin-3-ol, 7-Methyl-quinolin-3-ol, or 8-Methyl-quinolin-3-ol. As a further example, when $R_8$ is phenyl, the compound of formula (VI) may be 2-Phenyl-quinolin-3-ol, 4-Phenyl-quinolin-3-ol, 5-Phenyl-quinolin-3-ol, 6-Phenyl-quinolin-3-ol, 7-Phenyl-quinolin-3-ol, or 8-Phenyl-quinolin-3-ol.

In some embodiments, the catalyst may be a compound of formula (X),

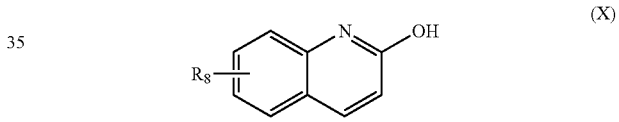

(X)

The $R_8$ may be as stated above. For example, when $R_8$ is H, the compound of formula (VI) may be quinolin-2-ol. As another example, when $R_8$ is methyl, the compound of formula (VI) may be 3-Methyl-quinolin-2-ol, 4-Methyl-quinolin-2-ol, 5-Methyl-quinolin-2-ol, 6-Methyl-quinolin-2-ol, 7-Methyl-quinolin-2-ol, or 8-Methyl-quinolin-2-ol. As a further example, when $R_8$ is phenyl, the compound of formula (VI) may be 3-Phenyl-quinolin-2-ol, 4-Phenyl-quinolin-2-ol, 5-Phenyl-quinolin-2-ol, 6-Phenyl-quinolin-2-ol, 7-Phenyl-quinolin-2-ol, or 8-Phenyl-quinolin-2-ol.

In accordance with the present disclosure, halobenzene (III) is etherified in the first step of the pathway shown in Scheme 1 with an alcohol of formula (IV) in the presence of a base and a catalyst. The catalyst may include a ligand and a copper compound. The catalyst may be a substituted oxamide of formula (V) or a substituted hydroxyquinoline of formula (VI), (VII), (VIII), (IX), or (X), and may be preferably a substituted oxamide of formula (Va) or a substituted oxamide of formula (Vb). The copper compound may be $Cu(acac)_2$, CuCl, CuBr, CuI, $CuCl_2$, $CuBr_2$, $CuI_2$, CuO, $Cu_2O$, CuOH, $Cu(OH)Cl$, $Cu(OH)_2$, CuS, $Cu_2S$, $Cu_2SO_3$, $CuSO_4$, $Cu_2P_2O_7$, $Cu_3(PO_4)_2$, CuSCN, $Cu(CO_2CH_3)_2$, $Cu(CO_2CH_3)_2 \cdot H_2O$, $Cu(CO_3)_2$, $Cu(NO_3)_2$, $Cu(NO)_2$, Nano-copper, CuO—ZnO, CuO—$Al_2O_3$, CuO—$Cr_2O_3$, $CuO/SiO_2$, Cu, Cu—Zn/Al, Cu—Zn—Zr, Cu—Cr, Cu—Zn—Al, CuMP, $CuX_nL_m$, or $Cu(phen)Cl_2$, or the like, or any combination thereof, and may be preferably $Cu(acac)_2$, CuCl, CuBr, CuI, or Cu, or any combination thereof. The base may be NaOH, KOH, K$_2$CO$_3$, Na$_2$CO$_3$, KTB, NaTB, LiOH, Cs$_2$CO$_3$, or a mixture of at least two of NaOH, KOH, K$_2$CO$_3$, Na$_2$CO$_3$, KTB, NaTB, LiOH, Cs$_2$CO$_3$, and may be preferably NaOH. In the reaction, the halobenzene (III) may be treated in an alcohol solvent of formula (IV) in the presence of the catalyst at room temperature, followed by being treated by the base at a temperature between 0° C. and 225° C., preferably at a temperature between 10° C. and 215° C., more preferably at a temperature between 20° C. and 205° C., more preferably at a temperature between 30° C. and 195° C., more preferably at a temperature between 40° C. and 185° C., more preferably at a temperature between 50° C. and 175° C., more preferably at a temperature between 60° C. and 165° C., more preferably at a temperature between 70° C. and 155° C., more preferably at a temperature between 80° C. and 145° C., more preferably at a temperature between 90° C. and 135° C., more preferably at a temperature between 100° C. and 125° C., more preferably at a temperature between 110° C. and 115° C., for a period (e.g., approximately 20-24 hours) until completed (<5% from the halobenzene (III) by High Performance Liquid Chromatography (HPLC), thin layer chromatography (TLC), or gas chromatography (GC)), to afford an ether compound of formula (II). In some embodiments, the molar yield of this reaction may be at least 40%, at least 45%, at least 50%, at least 55%, at least 60%, or at least 65%. In certain embodiments, the molar yield of this reaction may be at least 65%. In certain embodiments, the molar yield of this reaction may be at least 66%. In certain embodiments, the molar yield of this reaction may be in a range of 66-73%. In some embodiments, the exemplary methods of the current invention provide synthesizing routes for chromanone and chromanone derivatives that can avoid using phenol. In some embodiments, the exemplary methods of the current invention provides high yields while avoids using phenol.

The second step shown in Scheme 1 is the oxidation of the ether compound of formula (II) to generate an acid compound of formula (XI). In the reaction, the ether compound of formula (II) may be treated with Tempo in a solvent such as a mixture of acetonitrile and water in a ratio, preferably 3:2, at a temperature between 0° C. and 80° C., more preferably at a temperature between 10° C. and 70° C., more preferably at a temperature between 20° C. and 60° C., more preferably at a temperature between 30° C. and 50° C., more preferably at a temperature between 30° C. and 40° C., more preferably at a temperature between 33° C. and 35° C. The reaction mixture may be treated by sodium chlorite aqueous solution and sodium hypochlorite aqueous solution at the temperature between 0° C. and 80° C., more preferably at the temperature between 10° C. and 70° C., more preferably at the temperature between 20° C. and 60° C., more preferably at the temperature between 30° C. and 50° C., more preferably at the temperature between 30° C. and 40° C., more preferably at the temperature between 33° C. and 35° C., for a period (e.g., approximately 0.5 hours). Further, the sodium chlorite aqueous solution and sodium hypochlorite aqueous solution may be added dropwise to the reaction mixture at the temperature between 0° C. and 80° C., more preferably at the temperature between 10° C. and 70° C., more preferably at the temperature between 20° C. and 60° C., more preferably at the temperature between 30° C. and 50° C., more preferably at the temperature between 30° C. and 40° C., more preferably at the temperature between 33° C. and 35° C., for a period (e.g., approximately 2 hours) until completed (<5% from the ether compound of formula (II) by HPLC, TLC, or GC). This is followed by treatment with sodium dithionite at a temperature between 20° C. and 25° C., preferably about room temperature, for about 1 hour, to yield the acid compound of formula (XI). In some embodiments, the molar yield of this reaction may be at least 60%, at least 65%, at least 70%, at least 75%, at least 80%, or at least 85%. In certain embodiments, the molar yield of this reaction may be at least 85%. In certain embodiments, the molar yield of this reaction may be at least 66%. In certain embodiments, the molar yield of this reaction may be around 90%. In certain embodiments, the exemplary oxidation step of the current invention avoids using sulfuric acid. In some embodiments, the exemplary oxidation step of the current invention provides high yields while avoids sulfuric acid.

The acid compound of formula (XI) is dehydrated and cyclized in the third step of the pathway shown in Scheme 1 in the presence of an acid, preferably concentrated sulfuric acid. In the reaction, the acid compound of formula (XI) may be treated in an acid solvent such as concentrated sulfuric acid, at a temperature between 0° C. and 50° C., more preferably at a temperature between 10° C. and 40° C., more preferably at a temperature between 20° C. and 30° C., more preferably at a temperature between 20° C. and 25° C., more preferably about room temperature, for a period (e.g., approximately 20-24 hours) until completed (<5% from the acid compound of formula (XI) by HPLC, TLC, or GC), to yield a substituted chromanone derivative of formula (I). In some embodiments, the molar yield of this reaction may be at least 60%, at least 65%, at least 70%, at least 75%, at least 80%, or at least 85%. In certain embodiments, the molar yield of this reaction may be at least 85%. In certain embodiments, the molar yield of this reaction may be at least 66%. In certain embodiments, the molar yield of this reaction may be around 90%.

A method for preparing the compound of formula (I) may be illustrated in the following scheme 2.

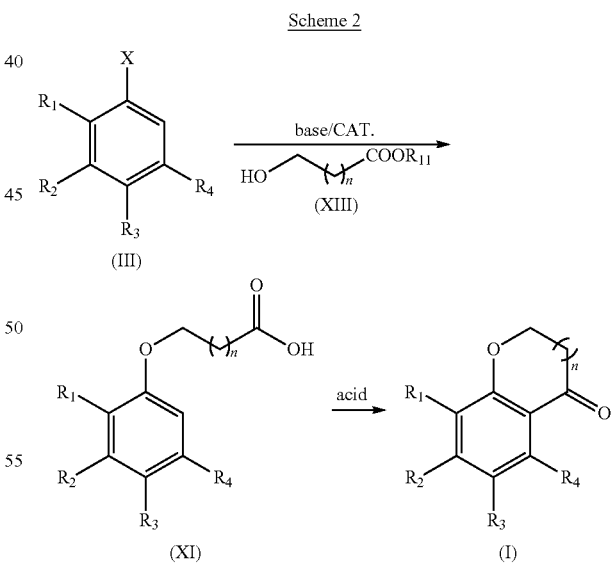

The compound of formula (I), the compound of formula (XI), and the process of preparing the compound of formula (I) from the compound of formula (XI) may be as stated above.

In a further aspect of the present disclosure, the compound of formula (XI) may be prepared by reacting the compound of formula (III) with a compound of formula (XIII)

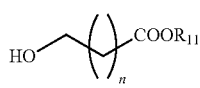

in the presence of a catalyst and a base. The compound of formula (III), the catalyst, and the base may be as stated above.

In the compound of formula (XIII), n may be as stated above for the process of preparing the compound of formula (I), and $R_{11}$ may be H, —$CH_3$, or —$CH_2CH_3$. In some embodiments, when n is 1 and $R_{11}$ is H, the compound of formula (XIII) may be 3-hydroxy-propionic acid. In certain preferred embodiments, when n is 1 and $R_{11}$ is —$CH_3$, the compound of formula (XIII) may be 3-hydroxy-propionic acid methyl ester. In certain preferred embodiments, when n is 1 and $R_{11}$ is —$CH_2CH_3$, the compound of formula (XIII) may be 3-hydroxy-propionic acid ethyl ester. In certain preferred embodiments, when n is 0 and $R_{11}$ is H, the compound of formula (XIII) may be hydroxy-acetic acid. In certain preferred embodiments, when n is 0 and $R_{11}$ is —$CH_3$, the compound of formula (XIII) may be hydroxy-acetic acid methyl ester. In certain preferred embodiments, when n is 0 and $R_{11}$ is —$CH_2CH_3$, the compound of formula XIII) may be hydroxy-acetic acid ethyl ester. In certain preferred embodiments, when n is 2 and $R_{11}$ is H, the compound of formula (XIII) may be 4-hydroxy-butyric acid. In certain preferred embodiments, when n is 3 and $R_{11}$ is H, the compound of formula (XIII) may be 5-hydroxy-pentanoic acid. In certain preferred embodiments, when n is 4 and $R_{11}$ is H, the compound of formula (XIII) may be 6-hydroxy-hexanoic acid. In certain preferred embodiments, when n is 5 and $R_{11}$ is H, the compound of formula (XIII) may be 7-hydroxy-heptanoic acid.

In accordance with the present disclosure, halobenzene (III) is etherified in the first step of the pathway shown in Scheme 2 with an alcohol of formula (XIII) in the presence of a base and a catalyst. The catalyst may include a ligand and a copper compound. The catalyst may be a substituted oxamide of formula (V) or a substituted hydroxyquinoline of formula (VI), (VII), (VIII), (IX), or (X), and may be preferably a substituted oxamide of formula (Va) or a substituted oxamide of formula (Vb). The copper compound may be $Cu(acac)_2$, CuCl, CuBr, CuI, $CuCl_2$, $CuBr_2$, $CuI_2$, CuO, $Cu_2O$, CuOH, $Cu(OH)Cl$, $Cu(OH)_2$, CuS, $Cu_2S$, $Cu_2SO_3$, $CuSO_4$, $Cu_2P_2O_7$, $Cu_3(PO_4)_2$, CuSCN, $Cu(CO_2CH_3)_2$, $Cu(CO_2CH_3)_2 \cdot H_2O$, $Cu(CO_3)_2$, $Cu(NO_3)_2$, $Cu(NO)_2$, Nano-copper, CuO—ZnO, CuO—$Al_2O_3$, CuO—$Cr_2O_3$, $CuO/SiO_2$, Cu, Cu—Zn/Al, Cu—Zn—Zr, Cu—Cr, Cu—Zn—Al, CuMP, CuXnLm, or $Cu(phen)Cl_2$, or the like, or any combination thereof, and may be preferably $Cu(acac)_2$, CuCl, CuBr, CuI, or Cu, or any combination thereof. The base may be NaOH, KOH, $K_2CO_3$, $Na_2CO_3$, KTB, NaTB, LiOH, $Cs_2CO_3$, or a mixture of at least two of NaOH, KOH, $K_2CO_3$, $Na_2CO_3$, KTB, NaTB, LiOH, $Cs_2CO_3$, and may be preferably NaOH. In the reaction, the halobenzene (III) may be treated in an alcohol solvent of formula (XIII) in the presence of the catalyst at room temperature, followed by being treated by the base at a temperature between 0° C. and 225° C., preferably at a temperature between 10° C. and 215° C., more preferably at a temperature between 20° C. and 205° C., more preferably at a temperature between 30° C. and 195° C., more preferably at a temperature between 40° C. and 185° C., more preferably at a temperature between 50° C. and 175° C., more preferably at a temperature between 60° C. and 165° C., more preferably at a temperature between 70° C. and 155° C., more preferably at a temperature between 80° C. and 145° C., more preferably at a temperature between 90° C. and 135° C., more preferably at a temperature between 100° C. and 125° C., more preferably at a temperature between 110° C. and 115° C., for a period (e.g., approximately 20-24 hours) until completed (<5% from the halobenzene (III) by HPLC, TLC, or GC), to afford the acid compound of formula (XI).

The process of preparing the compound of formula (I) in the second step of the pathway shown in Scheme 2 may be as stated above for the process of preparing the compound of formula (I) in the third step of the pathway shown in Scheme 1.

A method for preparing the compound of formula (I) may be illustrated in the following scheme 3:

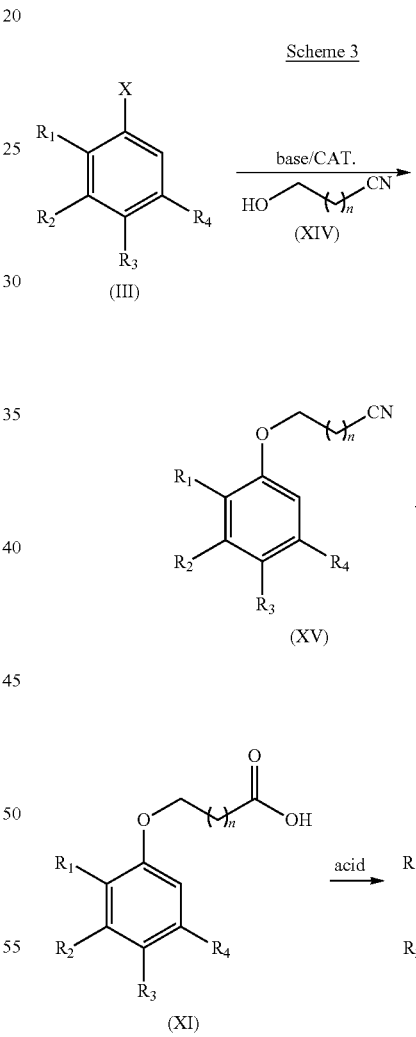

The compound of formula (I), the compound of formula (XI), and the process of preparing the compound of formula (I) from the compound of formula (XI) may be as stated above.

In a further aspect of the present disclosure, the compound of formula (XI) may be prepared by hydrolyzing the compound of formula (XV)

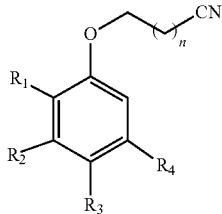

(XV)

in the presence of a base or an acid. In some embodiments, the base may be NaOH or KOH. In some embodiments, the acid may be concentrated sulfuric acid or concentrated hydrochloric acid.

In the process of preparing the compound of formula (XI), the n, $R_1$, $R_2$, $R_3$, and $R_4$ may be as stated above for the process of preparing the compound of formula (I). For example, when $R_1$ and $R_3$ are H, and $R_2$ and $R_4$ are the same groups, the compound of formula (XV) may be a compound of formula (XVa):

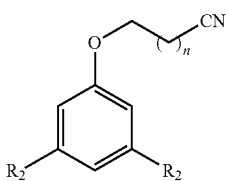

(XVa)

Preferably, when $R_1$ and $R_3$ are H, and $R_2$ and $R_4$ are F, the compound of formula (XV) may be a compound of formula (XVa$_1$):

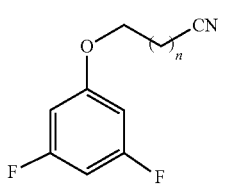

(XVa$_1$)

Preferably, when $R_1$ and $R_3$ are H, $R_2$ and $R_4$ are F, and n is 1, the compound of formula (XV) may be a compound of formula (XVa$_2$):

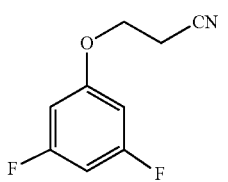

(XVa$_2$)

As another example, when $R_1$ and $R_3$ are H, and $R_2$ and $R_4$ are different groups, the compound of formula (XV) may be a compound of formula (XVb):

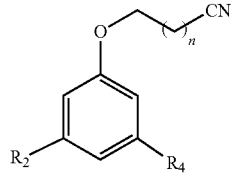

(XVb)

Preferably, when $R_1$ and $R_3$ are H, $R_2$ is Cl, and $R_4$ is F, the compound of formula (XV) may be a compound of formula (XVb$_1$):

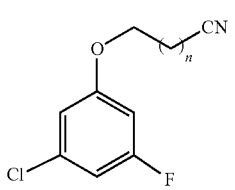

(XVb$_1$)

Preferably, when $R_1$ and $R_3$ are H, $R_2$ is Cl, $R_4$ is F, and n is 1, the compound of formula (XV) may be a compound of formula (XVb$_2$):

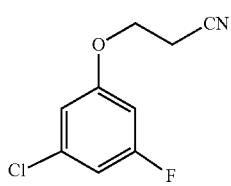

(XVb$_2$)

As a further example, when $R_1$, $R_2$, and $R_4$ are H, the compound of formula (XV) may be a compound of formula (XVc):

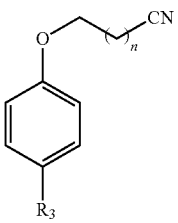

XVc

Preferably, when $R_1$, $R_2$, and $R_4$ are H, $R_3$ is F, the compound of formula (XV) may be a compound of formula (XVc$_1$):

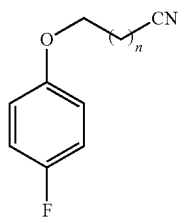

(XVc₁)

Preferably, when $R_1$, $R_2$, and $R_4$ are H, $R_3$ is F, and n is 1, the compound of formula (XV) may be a compound of formula (XVc₂):

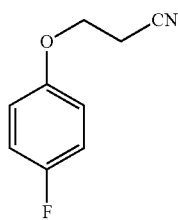

(XVc₂)

As a still further example, when $R_2$, $R_3$, and $R_4$ are H, the compound of formula(XV) may be a compound of formula (XVd):

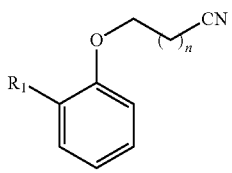

(XVd)

Preferably, when $R_2$, $R_3$, and $R_4$ are H, and $R_1$ is F, the compound of formula (XV) may be a compound of formula (XVd₁):

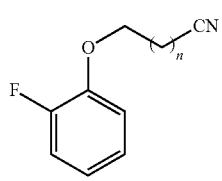

(XVd₁)

Preferably, when $R_2$, $R_3$, and $R_4$ are H, $R_1$ is F, and n is 1, the compound of formula(XV) may be a compound of formula (XVd₂):

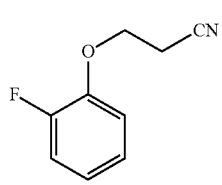

(XVd₂)

In a further aspect of the present disclosure, the compound of formula (XV) may be prepared by reacting the compound of formula (III),

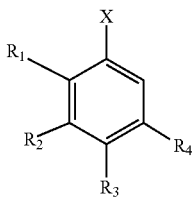

(III)

with a compound of formula (XIV)

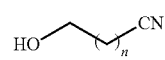

(XIV)

in the presence of a catalyst and a base. The compound of formula (III), the catalyst, and the base may be as stated above.

In the compound of formula (XIV), n may be as stated above for the process of preparing the compound of formula (I). In some embodiments, when n is 0, the compound of formula (XIV) may be hydroxy-acetonitrile. In certain preferred embodiments, when n is 1, the compound of formula (XIV) may be 3-hydroxy-propionitrile. In certain preferred embodiments, when n is 2, the compound of formula (XIV) may be 4-hydroxy-butyronitrile. In certain preferred embodiments, when n is 3, the compound of formula (XIV) may be 5-hydroxy-pentanenitrile. In certain preferred embodiments, when n is 4, the compound of formula (XIV) may be 6-hydroxy-hexanenitrile. In certain preferred embodiments, when n is 5, the compound of formula (XIV) may be 7-hydroxy-heptanenitrile.

In accordance with the present disclosure, halobenzene (III) is etherified in the first step of the pathway shown in Scheme 3 with an alcohol of formula (XIV) in the presence of a base and a catalyst. The catalyst may include a ligand and a copper compound. The catalyst may be a substituted oxamide of formula (V) or a substituted hydroxyquinoline of formula (VI), (VII), (VIII), (IX), or (X), and may be preferably a substituted oxamide of formula (Va) or a substituted oxamide of formula (Vb). The copper compound may be $Cu(acac)_2$, CuCl, CuBr, CuI, $CuCl_2$, $CuBr_2$, $CuI_2$, CuO, $Cu_2O$, CuOH, Cu(OH)Cl, $Cu(OH)_2$, CuS, $Cu_2S$, $Cu_2SO_3$, $CuSO_4$, $Cu_2P_2O_7$, $Cu_3(PO_4)_2$, CuSCN, $Cu(CO_2CH_3)_2$, $Cu(CO_2CH_3)_2·H_2O$, $Cu(CO_3)_2$, $Cu(NO_3)_2$, $Cu(NO)_2$, Nano-copper, CuO—ZnO, CuO—$Al_2O_3$, CuO—$Cr_2O_3$, $CuO/SiO_2$, Cu, Cu—Zn/Al, Cu—Zn—Zr, Cu—Cr, Cu—Zn—Al, CuMP, CuXnLm, or $Cu(phen)Cl_2$, or the like, or any combination thereof, and may be preferably $Cu(acac)_2$, CuCl, CuBr, CuI, or Cu, or any combination thereof. The base may be NaOH, KOH, $K_2CO_3$, $Na_2CO_3$, KTB, NaTB, LiOH, $Cs_2CO_3$, or a mixture of at least two of NaOH, KOH, $K_2CO_3$, $Na_2CO_3$, KTB, NaTB, LiOH, $Cs_2CO_3$, and is preferably NaOH. In the reaction, the halobenzene (III) may be treated in an alcohol solvent of formula (XIV) in the presence of the catalyst at room temperature, followed by being treated by the base at a temperature between 0° C. and 225° C., preferably at a temperature between 10° C. and 215° C., more preferably at a temperature between 20° C. and 205° C., more preferably at a temperature between 30° C. and 195° C., more preferably at a temperature between 40° C. and 185° C., more preferably at a temperature between 50° C. and 175° C., more preferably at a temperature between 60° C. and 165° C., more preferably at a temperature between 70° C. and 155° C., more preferably at a temperature between 80° C. and 145° C., more preferably at a temperature between 90° C. and 135° C., more preferably at a temperature between 100° C. and 125° C., more preferably at a temperature between 110° C. and 115° C., for a period (e.g., approximately 20-24 hours) until completed (<5% from the halobenzene (III) by HPLC, TLC, or GC), to afford a nitrile compound of formula (XV). The nitrile compound of formula (XV) is hydrolyzed in the second step of the pathway shown in Scheme 3 in the presence of concentrated sulfuric acid, concentrated hydrochloric acid, or nitrilase (e.g., Alcaligenes faecalis JM3, Pseudomonas putida MTCC5110, and Alcaligenes faecalis ZJUTB10), preferably nitrilase, more preferably concentrated hydrochloric acid. In the reaction, the concentrated hydrochloric acid may be added into the nitrile compound of formula (XV), at a temperature between 0° C. and 200° C., preferably at a temperature between 10° C. and 190° C., more preferably at a temperature between 20° C. and 180° C., more preferably at a temperature between 30° C. and 170° C., more preferably at a temperature between 40° C. and 160° C., more preferably at a temperature between 50° C. and 150° C., more preferably at a temperature between 60° C. and 140° C., more preferably at a temperature between 70° C. and 130° C., more preferably at a temperature between 80° C. and 120° C., more preferably at a temperature between 90° C. and 110° C., more preferably at a temperature between 95° C. and 100° C., for a period (e.g., approximately 4 hours until completed (<5% from the nitrile compound of formula (XV) by HPLC, TLC, or GC), to yield the acid compound of formula (XI).

The process of preparing the compound of formula (I) in the third step of the pathway shown in Scheme 3 may be as stated above for the process of preparing the compound of formula (I) in the third step of the pathway shown in Scheme 1.

A solvent for preparing the substituted chromanone derivatives may include but not limited to organic solvents such as nitriles, ethers, ketones, aromatic compounds, esters, amides, or the like, or any combination thereof. In some embodiments, the solvent may be dimethyl sulfoxide (DMSO), N,N-Dimethylformamide (DMF), N,N-Dimethylacetamide (DMA), N-Methyl pyrrolidone (NMP), acetonitrile, 1,4-dioxane, tetrahydrofuran (THF), Me-THF, cyclopentyl methyl ether, or the like, or any combination thereof. In certain preferred embodiments, the solvent may not be present. In certain preferred embodiments, the solvent may be DMSO, DMF, DMA, NMP, or the like, or any combination thereof. In certain preferred embodiments, the solvent may be a mixture of several solvents, e.g., a mixture of at least two of DMSO, DMF, DMA, NMP, acetonitrile, 1,4-dioxane, THF, Me-THF, or cyclopentyl methyl ether. The solvent may be chosen according to a reactant solubility, a temperature of the reaction, and chemical reactivity of the solvent, etc. In fact, any solvent which can dissolve the reaction raw materials may be used as a reaction solvent.

The stirring method used in preparing the substituted chromanone derivatives may be a mechanical or magnetic stirring method in which the reactants can be sufficiently contacted.

The addition of the reactant solution may be manually dropping or dropping using a mechanical drip machine, and the dropping speed may be constant or may be continuously changed as the reaction progresses.

As for separation of the final product, different separation methods may be used according to different forms of the final product, as a non-precipitate, the final product can be purified by extraction or distillation; as a precipitate, the final product can be purified by centrifugation, filtration, or the like.

In a further aspect of the present disclosure, the compound of formula (I) may be further treated to prepare a compound of formula (XII)

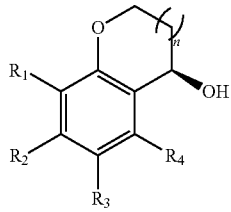

(XII)

or an enantiomer of the compound of formula (XII), in the presence of a hydrogen donor and a catalyst. In some embodiments, n, $R_1$, $R_2$, $R_3$, and $R_4$ are as defined above. In some embodiments, the hydrogen donor may be formic acid, formic acid metal salt, formic acid ammonium salt, or a mixture of formic acid and amine. In certain preferred embodiments, the hydrogen donor may be the mixture of formic acid and amine. In certain preferred embodiments, the hydrogen donor may be formic acid and triethylamine or formic acid and diisopropylethylamine. In some embodiments, the catalyst may be a ruthenium compound. In certain preferred embodiments, the catalyst may be RuCl(p-cymene)[(R,R)-Ts-DPEN] or RuCl(p-cymene)[(S,S)-Ts-DPEN].

The present disclosure may be illustrated by the following examples, but is not limited to the details thereof.

Example 1

3-(3,5-Difluoro-Phenoxy)-Propan-1-ol

To a solution of 1-Bromo-3,5-difluorobenzene (77.2 g, 400 mmol), Cu(acac)$_2$ (2.6 g, 10 mmol), and a ligand (5-tert-Butyl-quinolin-8-ol, 3.3 g, 16.4 mmol) in 290 g propylene glycol at ambient temperature was added NaOH (33.7 g, 842.5 mmol). The mixture was stirred and heated to 110° C. to 115° C. and refluxed at 110° C. to 115° C. for 20 hours to 24 hours until completed (<0.5% from 1-Bromo-3,5-difluorobenzene by gas chromatography (GC)). Then, the mixture was cooled to ambient temperature. 270 g water was added and the mixture was extracted by adding DCM (270 g). The water layer was separated and further extracted by adding DCM (135 g). The organic layers were combined and concentrated to an earthy yellow oil which weighted 49.4 g (65.7% molar yield).

Example 2

3-(3,5-Difluoro-Phenoxy)-Propionic Acid

A solution of the product (50 g) obtained in example 1 and Tempo (2.9 g, 18.6 mmol) in a solution of acetonitrile (300 mL) and water (200 mL) was warmed to approximately 35° C. To the mixture, was added a quarter (approximately 44 mL) sodium chlorite solution (formed by mixing 100 mL water and 75 g (829.3 mmol) sodium chlorite) and a quarter (approximately 10 mL) sodium hypochlorite solution (formed by mixing 30 mL water and 8.8 g (118.2 mmol) sodium hypochlorite) while maintaining a temperature at 33° C. to 35° C. The mixture was stirred at 33° C. to 35° C. for approximately 0.5 hours. To the mixture, was then slowly dropwise added remaining sodium chlorite solution and sodium hypochlorite solution using a dropping funnel under stirring at the temperature of 33° C. to 35° C., respectively. After the dropwise addition was completed (approximately 2 hours), the reaction was stirred at 33° C. to 35° C. for approximately 6 hours until completed (by thin layer chromatography (TLC)). Then, the mixture was cooled to a temperature of 20° C. to 25° C. Sodium dithionite (30 g, 172.4 mmol) was added and the mixture was stirred at the temperature of 20° C. to 25° C. for approximately 1 hour, and extracted by adding DCM (200 mL). The water layer was separated and further extracted by adding DCM (100 mL). The organic layers were combined, washed with water (50 mL), and concentrated to an earthy yellow oil which solidified on standing and weighted 48-50 g (90% molar yield).

Example 3

5,7-Difluoro-4-Chromanone

A mixture of the product (50 g) obtained in example 2 and concentrated sulfuric acid (150 g) was stirred at a temperature of 20° C. to 30° C. for 20 hours to 24 hours until completed (by TLC). The mixture was cooled to a temperature of 5° C. to 10° C. and slowly added dropwise to ice water (300 mL) under stirring at a temperature less 30° C. After the dropwise addition was completed, the mixture was stirred at 20° C. to 25° C. for approximately 0.5 hours. Then, the mixture was extracted by adding DCM (200 mL). The water layer was separated and further extracted by adding DCM (100 mL). The organic layers were combined. Then, an aqueous solution of sodium carbonate (5 g Na$_2$CO$_3$) was added and the mixture was stirred for approximately 1 hour. The organic layer was separated and washed with water (50 mL). Further, hydrochloric acid was added and the mixture was stirred for approximately 0.5 hours until the PH was 3-4. The aqueous layer was removed and the organic layer was concentrated to an earthy yellow oil under vacuum to afford 5,7-Difluoro-4-chromanone (90% molar yield).

The foregoing is a further detailed description of embodiments of the present disclosure in conjunction with examples, which facilitates those skilled in the art to readily understand and apply the substituted chromanone derivatives provided by the embodiments of the present disclosure, and the embodiments of the present disclosure are not limiting. It should be noted that, without departing from the spirit of the embodiments of the present disclosure, other modifications or improvements may occur and are intended to those skilled in the art, and are within the scope of the present disclosure defined by the claims.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

We claim:
1. A method for preparing a compound of formula (I):

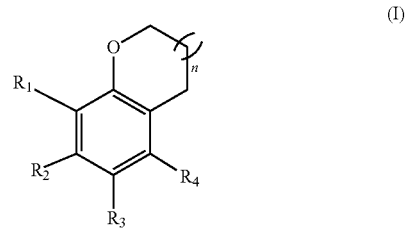

wherein n is 0 to 5, each of $R_1$, $R_2$, $R_3$, and $R_4$ being independently selected from the group consisting of H, —O-Alkyl, halo, alkyl, —CN, or —NO$_3$, and the method comprises:
treating a compound of formula (III),

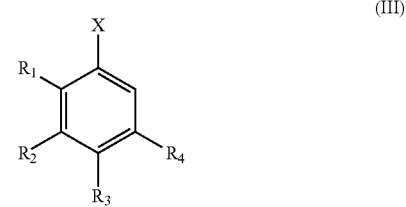

wherein X is halo, with a compound of formula (IV),

wherein $R_5$ is H, —$CH_3$, or —$CH_2CH_3$, in the presence of a catalyst and a base, wherein the catalyst includes a ligand and a copper compound, to obtain a compound of formula (II);

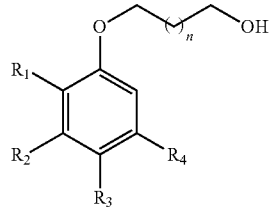

(II)

oxidizing the compound of formula (II) in the presence of an oxidant to obtain a compound of formula (XI); and

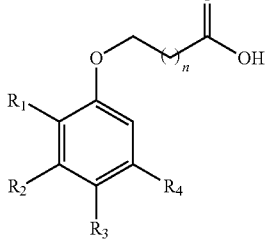

(XI)

treating the compound of formula (XI) with an acid to obtain the compound of formula (I).

2. The method of claim 1, wherein the copper compound is copper(II) acetylacetonate, CuCl, CuBr, CuI, $CuCl_2$, $CuBr_2$, $CuI_2$, CuO, $Cu_2O$, CuOH, Cu(OH)Cl, $Cu(OH)_2$, CuS, $Cu_2S$, $Cu_2SO_3$, $CuSO_4$, $Cu_2P_2O_7$, $Cu_3(PO_4)_2$, CuSCN, $Cu(CO_2CH_3)_2$, $Cu(CO_2CH_3)_2 \cdot H_2O$, $Cu(CO_3)_2$, $Cu(NO_3)_2$, $Cu(NO)_2$, Nano-copper, CuO—ZnO, CuO—$Al_2O_3$, CuO—$Cr_2O_3$, $CuO/SiO_2$, Cu, Cu—Zn/Al, Cu—Zn—Zr, Cu—Cr, Cu—Zn—Al, or Cu(phenanthroline)$Cl_2$, or a mixture of at least two of copper(II) acetylacetonate, CuCl, CuBr, CuI, $CuCl_2$, $CuBr_2$, $CuI_2$, CuO, CuzO, CuOH, Cu(OH)Cl, $Cu(OH)_2$, CuS, $Cu_2S$, $Cu_2SO_3$, $CuSO_4$, $Cu_2P_2O_7$, $Cu_3(PO_4)_2$, CuSCN, $Cu(CO_2CH_3)_2$, $Cu(CO_2CH_3)_2 \cdot H_2O$, $Cu(CO_3)_2$, $Cu(NO_3)_2$, $Cu(NO)_2$, Nano-copper, CuO—ZnO, CuO—$Al_2O_3$, CuO—$Cr_2O_3$, $CuO/SiO_2$, Cu, Cu—Zn/Al, Cu—Zn—Zr, Cu—Cr, Cu—Zn—Al, or Cu(phenanthroline)$Cl_2$.

3. The method of claim 1, wherein the ligand is a compound of formula (V),

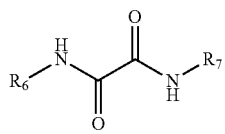

(V)

wherein each of $R_6$ and $R_7$ is independently selected from the group consisting of H, alkyl, and aryl, and the aryl is independently selected from the group consisting of phenyl, thienyl, pyrrolyl, substituted phenyl, hydroxyphenyl, and substituted phenol.

4. The method of claim 1, wherein the ligand is a compound of formula (Va)

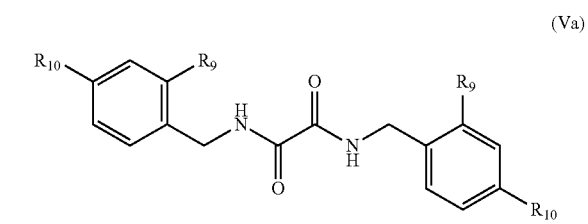

(Va)

or a compound of formula (Vb),

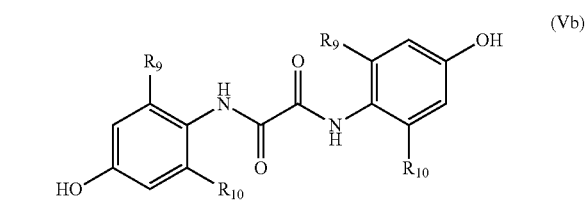

(Vb)

wherein each of $R_9$ and $R_{10}$ is independently selected from the group consisting of H, and alkyl.

5. The method of claim 1, wherein the ligand is a compound of formula (VI),

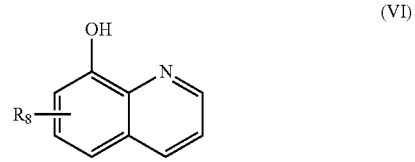

(VI)

a compound of formula (VII),

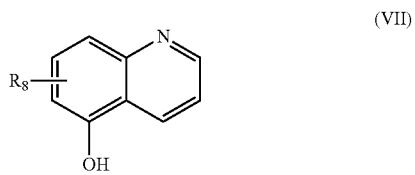

(VII)

a compound of formula (VIII),

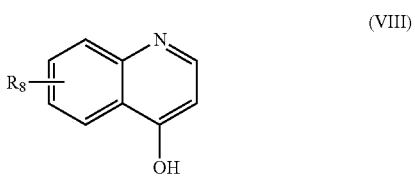

(VIII)

a compound of formula (IX),

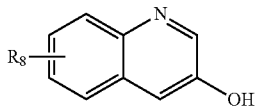

or a compound of formula (X),

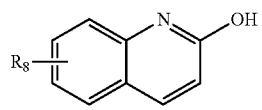

wherein $R_8$ is H, alkyl, or aryl.

6. The method of claim 1, wherein the base is NaOH, KOH, $K_2CO_3$, $Na_2CO_3$, KTB, NaTB, LiOH, $Cs_2CO_3$, or a mixture of at least two of NaOH, KOH, $K_2CO_3$, $Na_2CO_3$, KTB, NaTB, LiOH, or $Cs_2CO_3$.

7. The method of claim 1, wherein $R_1$ and $R_3$ are H, and $R_2$ and $R_4$ are the same halo.

8. The method of claim 1, wherein $R_1$, $R_2$, and $R_4$ are H, and $R_3$ is halo.

9. The method of claim 1, wherein $R_2$, $R_3$, and $R_4$ are H, and $R_1$ is halo.

10. The method of claim 1, wherein the oxidant includes at least one of 2,2,6,6-tetramethyl-1-piperidinyloxy (TEMPO), NaClO, or $NaClO_2$.

11. The method of claim 1, wherein the acid includes concentrated sulfuric acid.

12. A method for preparing a compound of formula (Ia3),

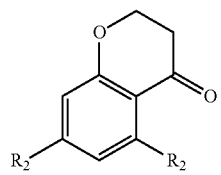

wherein $R_2$ is halo, and the method comprises:
treating a compound of formula (IIIa$_1$),

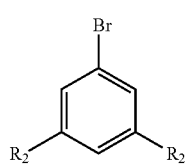

with 1,3-Propanediol in the presence of a catalyst and a base, to obtain a compound of formula (IIa3);

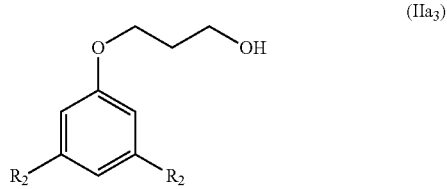

oxidizing the compound of formula (IIa3) in the presence of an oxidant to obtain a compound of formula (XIa3); and

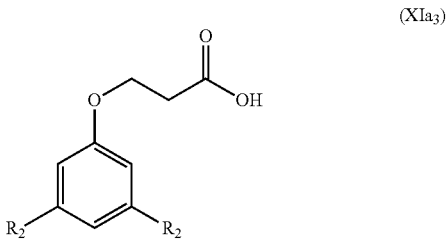

treating the compound of formula (XIa3) with an acid to obtain the compound of formula (Ia3).

13. The method of claim 12, wherein the catalyst includes a ligand and a copper compound.

14. The method of claim 12, wherein the oxidant includes at least one of 2,2,6,6-tetramethyl-1-piperidinyloxy (TEMPO), NaClO, or $NaClO_2$.

15. The method of claim 12, wherein the acid includes concentrated sulfuric acid.

16. The method of claim 13, wherein the ligand is oxalamide, substituted oxalamide, hydroxyquinoline, or substituted hydroxyquinoline.

17. The method of claim 16, wherein the copper compound is copper(II) acetylacetonate.

18. The method of claim 12, wherein $R_2$ is F.

19. The method of claim 12, wherein the method further comprises:
treating the compound of formula (Ia3) with a hydrogen donor in the presence of a catalyst to obtain a compound of

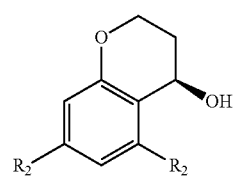

or an enantiomer thereof, wherein the hydrogen donor is formic acid, formic acid metal salt, formic acid ammonium salt, or a mixture of formic acid and amine, and the catalyst that is used to obtain the compound of

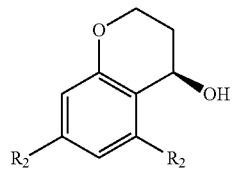
or the enantiomer thereof is a ruthenium compound.
* * * * *

UNITED STATES PATENT AND TRADEMARK OFFICE
CERTIFICATE OF CORRECTION

PATENT NO.         : 12,139,468 B2
APPLICATION NO.    : 17/807389
DATED              : November 12, 2024
INVENTOR(S)        : Gaofeng Bian et al.

Page 1 of 1

It is certified that error appears in the above-identified patent and that said Letters Patent is hereby corrected as shown below:

In the Claims

Column 40, Lines 32-43, formula (I):

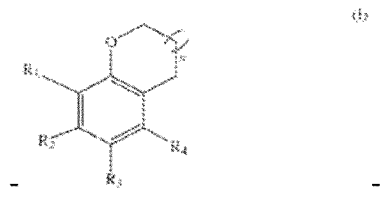

Should read:

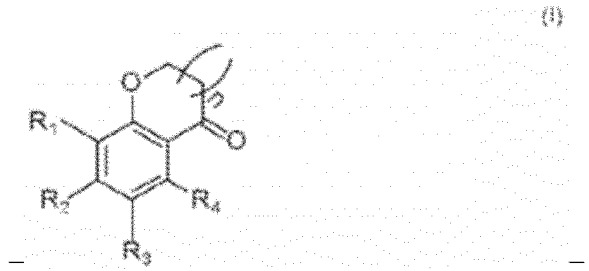

Signed and Sealed this
Twenty-fourth Day of December, 2024

Derrick Brent
*Acting Director of the United States Patent and Trademark Office*